(12) United States Patent
Lois et al.

(10) Patent No.: US 7,873,479 B2
(45) Date of Patent: Jan. 18, 2011

(54) METHODS OF DIAGNOSING INFLAMMATORY BOWEL DISEASE

(75) Inventors: Augusto Lois, San Diego, CA (US); Bruce Neri, Carlsbad, CA (US)

(73) Assignee: Prometheus Laboratories Inc., San Diego, CA (US)

( * ) Notice: Subject to any disclaimer, the term of this patent is extended or adjusted under 35 U.S.C. 154(b) by 650 days.

(21) Appl. No.: 11/565,544

(22) Filed: Nov. 30, 2006

(65) Prior Publication Data

US 2008/0131439 A1 Jun. 5, 2008

Related U.S. Application Data

(60) Provisional application No. 60/934,919, filed on Dec. 1, 2005.

(51) Int. Cl.
G06F 7/00 (2006.01)
(52) U.S. Cl. .............................. 702/19; 702/20; 703/11; 703/13; 707/700; 436/501
(58) Field of Classification Search ........................ None
See application file for complete search history.

(56) References Cited

U.S. PATENT DOCUMENTS

| 5,750,355 | A | 5/1998 | Targan et al. |
|---|---|---|---|
| 5,916,748 | A | 6/1999 | Targan et al. |
| 5,932,429 | A | 8/1999 | Targan et al. |
| 6,033,864 | A | 3/2000 | Braun et al. |
| 6,074,835 | A | 6/2000 | Braun et al. |
| 6,218,129 | B1 | 4/2001 | Walsh et al. |
| 6,309,643 | B1 | 10/2001 | Braun et al. |
| 2003/0204507 | A1 | 10/2003 | Li et al. |
| 2004/0043931 | A1 | 3/2004 | Hersberg et al. |
| 2004/0242972 | A1 | 12/2004 | Adak et al. |
| 2005/0054021 | A1 | 3/2005 | Targan et al. |
| 2005/0060295 | A1 * | 3/2005 | Gould et al. ................... 707/3 |
| 2005/0164929 | A1 | 7/2005 | Alvarez et al. |

FOREIGN PATENT DOCUMENTS

| WO | WO 98137415 | 8/1998 |
|---|---|---|
| WO | WO 01/89361 A2 | 11/2001 |
| WO | WO 03/053220 A2 | 7/2003 |
| WO | WO 2004/037073 | 5/2004 |
| WO | WO 2004/048600 | 6/2004 |

OTHER PUBLICATIONS

Reumaux, Dominque; Best Practice and Research Clinical Gastroenterology; Serological Markers in Inflammatory Bowel Disease; Feb. 2003; vol. 17(1); pp. 19-35.
Dubinsky, Maria C.; Clinical Utility of Serodiagnostic Testing in Suspect Pediatric Inflammatory Bowel Disease; The American Journal of Gastroenterology; vol. 96(3) 2001; pp. 758-765.
Arnott, et al., Sero-Reactivity to Microbial Components in Crohn's Disease is Associated with Disease Severity and Progression, but not NOD2/CARD15 Genotype; American Journal of Gastroenterology; 2004; 99:2376-2384; Blackwell Publishing.
Nakamura, R.M. et al. "Advances in clinical laboratory tests for inflammatory bowel disease." *Clinica Chimica Acta* (2003), vol. 335, pp. 9-20.
Restriction Requirement mailed on Jun. 22, 2010 for U.S. Appl. No. 11/841,699, filed Aug. 20, 2007, 6 pages.
Augusto et al. "Development of a hybrid algorithm based on learning classifiers that improves diagnosis of inflammatory bowel disease and differentiation between Crohn's and ulcerative colitis in a six-marker system" Gastroenterology, 2006, vol. 130, No. 4, Suppl. 2, p. A323. XP009115454.
Vernier et al. "Relevance of Serologic Studies in Inflammatory Bowel Disease," Current Gastroenterology Reports, 2004, vol. 6, No. 6, pp. 482-487. XP009115628.
Zhao et al. "Entity identification for heterogeneous database integration—a multiple classifier system approach and empirical evaluation," Information Systems 2005, vol. 30, No. 2, pp. 119-132. XP025366573.
Targan, S.R., Landers, C.J., Yang, H. et al., "Antibodies to CBir1 flagellin define a unique response that is associated independently with complicated Crohn's disease," *Gastroenterology*, 2005; 128:2020-2028.
Abreu, M.T. et al., "Use of serologic tests in Crohn's disease," *Clin Perspect Gastroenterol*, 2001; 155-164.
Fleshner, P.R., Vasiliauskas, E.A., Kam, L.Y. et al., "High level perinuclear antineutrophil cytoplasmic antibody (pANCA) in ulcerative colitis patients before colectomy predicts the development of chronic pouchitis after ileal pouch-anal anastomosis," *Gut.*, 2001; 49(5):671-677.
Vasiliauskas, E.A., Kam, L.Y., Karp, L.C. et al., "Marker antibody expression stratifies Crohn's disease into immunologically homogenous subgroups with distinct clinical characteristics Vasiliauskas," *Gut.*, 2000; 47(4):487-496.
Targan, S.R., "The Utility of ANCA and ASCA in Inflammatory bowel disease," *Inflamm Bowel Dis.*, 1999; 5(1):61-3.
Ruemele, F.M., Targan, S.R., Levy, G. et al., "Diagnostic accuracy of serological assays in pediatric inflammatory bowel disease," *Gastroenterology*, 1998; 115(4):822-829.

* cited by examiner

*Primary Examiner*—Mary K Zeman
(74) *Attorney, Agent, or Firm*—Townsend and Townsend and Crew LLP

(57) ABSTRACT

The present invention provides methods, systems, and code for accurately classifying whether a sample from an individual is associated with inflammatory bowel disease (IBD) or a clinical subtype thereof. In particular, the present invention is useful for classifying a sample from an individual as an IBD sample using a statistical algorithm and/or empirical data. The present invention is also useful for differentiating between a clinical subtype of IBD such as Crohn's disease (CD) and ulcerative colitis (UC) using a statistical algorithm and/or empirical data. Thus, the present invention provides an accurate diagnostic prediction of IBD or a clinical subtype thereof and prognostic information useful for guiding treatment decisions.

33 Claims, 4 Drawing Sheets

| | 2<br>Omp-C | 3<br>ASCA-IgA | 4<br>ASCA-IgG | 5<br>Cbir1 | 6<br>pANCA | 7<br>Non-IBD/IBD | 8<br>Diagnosis | 9<br>Probability for 0 | 10<br>Probability for 1 | 11<br>Probability for 2 |
|---|---|---|---|---|---|---|---|---|---|---|
| SG07222043 | 2.9 | 1.4 | 3.5 | 8.669 | 0 | 0 | 0 | 0.73881 | 0.09701 | 0.16418 |
| SG07222005 | 0.9 | 2.2 | 2.3 | 5.92 | 0 | 0 | 0 | 0.73881 | 0.09701 | 0.16418 |
| SE11061100 | 7.5 | 1.4 | 3.5 | 9.60099437 | 0 | 0 | 0 | 0.73881 | 0.09701 | 0.16418 |
| SG07222028 | 5.2 | 2.6 | 2.9 | 3.939 | 1 | 0 | 0 | 0.41379 | 0.10345 | 0.48276 |
| SG07222010 | 1.8 | 2.6 | 10 | 3.97 | 0 | 0 | 0 | 0.73881 | 0.09701 | 0.16418 |
| SE11061064 | 8.7 | 24 | 12.7 | 56.3576681 | 0 | 0 | 0 | 0.38462 | 0.61538 | 0.00000 |
| SE11061062 | 3.4 | 3.7 | 3.4 | 4.56971632 | 0 | 0 | 0 | 0.73881 | 0.09701 | 0.16418 |
| SG07222118 | 7.7 | 13.8 | 4.1 | 3.18 | 0 | 0 | 0 | 0.73881 | 0.09701 | 0.16418 |
| SE11061094 | 16.6 | 2.3 | 4.7 | 15.1623933 | 0 | 0 | 0 | 0.17500 | 0.52500 | 0.30000 |
| SE11061084 | 2.8 | 0.4 | 0.9 | 4.38862403 | 1 | 0 | 0 | 0.73881 | 0.09701 | 0.16418 |
| SE11061045 | 8.9 | 2.3 | 4.8 | 8.490928 | 0 | 0 | 0 | 0.41379 | 0.10345 | 0.48276 |
| SE11061089 | 8 | 5.6 | 4 | 5.62521943 | 0 | 0 | 0 | 0.73881 | 0.09701 | 0.16418 |
| SE11061121 | 5.3 | 2 | 6.3 | 4.24191095 | 0 | 0 | 0 | 0.73881 | 0.09701 | 0.16418 |
| SE11061054 | 7.2 | 5 | 2 | 8.53797967 | 0 | 0 | 0 | 0.73881 | 0.09701 | 0.16418 |
| SE11061120 | 19.1 | 7.8 | 2.5 | 6.93804629 | 0 | 0 | 0 | 0.38298 | 0.14894 | 0.46809 |
| SE11061071 | 6.8 | 4.1 | 3.1 | 25.8155087 | 0 | 0 | 0 | 0.38462 | 0.61538 | 0.00000 |
| SE11061109 | 6 | 4.1 | 10 | 5.90331709 | 0 | 0 | 0 | 0.73881 | 0.09701 | 0.16418 |
| SE11061068 | 8.5 | 4.5 | 1.9 | 8.90373603 | 0 | 0 | 0 | 0.73881 | 0.09701 | 0.16418 |
| SE11061046 | 17 | 5.2 | 3.6 | 10.215401 | 0 | 0 | 0 | 0.38298 | 0.14894 | 0.46809 |
| SE11061081 | 7.6 | 12.2 | 4.3 | 20.3574337 | 0 | 0 | 0 | 0.73881 | 0.09701 | 0.16418 |
| SE11061053 | 3.9 | 1.6 | 4.5 | 2.84695275 | 0 | 0 | 0 | 0.73881 | 0.09701 | 0.16418 |
| SE11061059 | 5 | 3.6 | 4.9 | 10.1350871 | 0 | 0 | 0 | 0.73881 | 0.09701 | 0.16418 |
| SG07222014 | 6.3 | 2.3 | 1.7 | 4.573 | 0 | 0 | 0 | 0.73881 | 0.09701 | 0.16418 |
| SE11061122 | 14.2 | 8 | 15 | 4.42659557 | 0 | 0 | 0 | 0.38298 | 0.14894 | 0.46809 |
| SE11061098 | 22.2 | 2.1 | 5.5 | 3.15207823 | 0 | 0 | 0 | 0.38298 | 0.14894 | 0.46809 |
| SG07222069 | 2.5 | 2.2 | 6 | 4.272 | 0 | 0 | 0 | 0.02239 | 0.08209 | 0.89552 |
| SE11061104 | 6.4 | 2 | 2.3 | 3.69989175 | 0 | 0 | 0 | 0.73881 | 0.09701 | 0.16418 |
| SE11061079 | 2.9 | 2 | 1.7 | 6.70632345 | 0 | 0 | 0 | 0.73881 | 0.09701 | 0.16418 |
| SG07222100 | 0.1 | 0.9 | 6.6 | 11.863 | 0 | 0 | 0 | 0.73881 | 0.09701 | 0.16418 |

*FIG. 4*

METHODS OF DIAGNOSING INFLAMMATORY BOWEL DISEASE

CROSS-REFERENCE TO RELATED APPLICATIONS

This application claims priority to U.S. application Ser. No. 11/293,616, filed Dec. 1, 2005, the teaching of which is hereby incorporated by reference in its entirety for all purposes.

BACKGROUND OF THE INVENTION

Inflammatory bowel disease (IBD), which occurs worldwide and afflicts millions of people, is the collective term used to describe three gastrointestinal disorders of unknown etiology: Crohn's disease (CD), ulcerative colitis (UC), and indeterminate colitis (IC). IBD, together with irritable bowel syndrome (IBS), will affect one-half of all Americans during their lifetime, at a cost of greater than $2.6 billion dollars for IBD and greater than $8 billion dollars for IBS. A primary determinant of these high medical costs is the difficulty of diagnosing digestive diseases. The cost of IBD and IBS is compounded by lost productivity, with people suffering from these disorders missing at least 8 more days of work annually than the national average.

Inflammatory bowel disease has many symptoms in common with irritable bowel syndrome, including abdominal pain, chronic diarrhea, weight loss, and cramping, making definitive diagnosis extremely difficult. Of the 5 million people suspected of suffering from IBD in the United States, only 1 million are diagnosed as having IBD. The difficulty in differentially diagnosing IBD and IBS hampers early and effective treatment of these diseases. Thus, there is a need for rapid and sensitive testing methods for definitively distinguishing IBD from IBS.

Although progress has been made in precisely diagnosing clinical subtypes of IBD, current methods for diagnosing an individual as having either Crohn's disease, ulcerative colitis, or indeterminate colitis are relatively costly and require labor-intensive clinical, radiographic, endoscopic, and/or histological techniques. These costly techniques may be justified for those individuals previously diagnosed with or strongly suggested to have IBD, but a less expensive and highly sensitive alternative would be advantageous for first determining if an individual even has IBD. For example, such a highly sensitive screening assay would provide physicians with an inexpensive means for rapidly distinguishing individuals with IBD from those having IBS, thereby facilitating earlier and more appropriate therapeutic intervention and minimizing uncertainty for patients and their families. The highly sensitive screening assay could also be used to differentiate between clinical subtypes of IBD or could be combined with a subsequent, highly specific assay for determining if an individual diagnosed with IBD has either Crohn's disease, ulcerative colitis, or indeterminate colitis.

Unfortunately, highly sensitive and inexpensive screening assays for distinguishing IBD from other digestive diseases presenting with similar symptoms and for differentiating between clinical subtypes of IBD are currently not available. Thus, there is a need for improved methods of diagnosing IBD at a very early stage of disease progression and for stratifying IBD into a clinical subtype such as Crohn's disease, ulcerative colitis, or indeterminate colitis. The present invention satisfies these needs and provides related advantages as well.

BRIEF SUMMARY OF THE INVENTION

The present invention provides methods, systems, and code for accurately classifying whether a sample from an individual is associated with inflammatory bowel disease (IBD) or a clinical subtype thereof such as Crohn's disease (CD), ulcerative colitis (UC), or indeterminate colitis (IC). As a non-limiting example, the present invention is useful for classifying a sample from an individual as an IBD sample using a statistical algorithm and/or empirical data. The present invention is also useful for differentiating between CD and UC using a statistical algorithm and/or empirical data. Thus, the present invention provides an accurate diagnostic prediction of IBD or a clinical subtype thereof and prognostic information useful for guiding treatment decisions.

In one aspect, the present invention provides a method for classifying whether a sample from an individual is associated with IBD, the method comprising:
 (a) determining the presence or level of at least one marker selected from the group consisting of an anti-neutrophil antibody, anti-*Saccharomyces cerevisiae* antibody, anti-microbial antibody, and combinations thereof in the sample; and
 (b) classifying the sample as an IBD sample or non-IBD sample using a statistical algorithm based upon the presence or level of the at least one marker.

In a related aspect, the present invention provides a method for classifying whether a sample from an individual is associated with a clinical subtype of IBD, the method comprising:
 (a) determining the presence or level of at least one marker selected from the group consisting of an anti-neutrophil antibody, anti-*Saccharomyces cerevisiae* antibody, anti-microbial antibody, and combinations thereof in the sample; and
 (b) classifying the sample as a CD sample, UC sample, or non-IBD sample using a statistical algorithm based upon the presence or level of the at least one marker.

In another aspect, the present invention provides a method for monitoring the progression or regression of IBD in an individual, the method comprising:
 (a) determining the presence or level of at least one marker selected from the group consisting of an anti-neutrophil antibody, anti-*Saccharomyces cerevisiae* antibody, anti-microbial antibody, and combinations thereof in a sample from the individual; and
 (b) determining the presence or severity of IBD in the individual using a statistical algorithm based upon the presence or level of the at least one marker.

In a related aspect, the present invention provides a method for monitoring drug efficacy in an individual receiving a drug useful for treating IBD, the method comprising:
 (a) determining the presence or level of at least one marker selected from the group consisting of an anti-neutrophil antibody, anti-*Saccharomyces cerevisiae* antibody, anti-microbial antibody, and combinations thereof in a sample from the individual; and
 (b) determining the presence or severity of IBD in the individual using a statistical algorithm based upon the presence or level of the at least one marker.

In yet another aspect, the present invention provides a computer-readable medium including code for controlling one or more processors to classify whether a sample from an individual is associated with IBD, the code including instructions to apply a statistical process to a data set indicating the presence or level of at least one marker selected from the group consisting of an anti-neutrophil antibody, anti-*Saccha-* romyces cerevisiae antibody, antimicrobial antibody, and combinations thereof in the sample to produce a statistically derived decision classifying the sample as an IBD sample or non-IBD sample based upon the presence or level of the at least one marker.

In a related aspect, the present invention provides a computer-readable medium including code for controlling one or more processors to classify whether a sample from an individual is associated with a clinical subtype of IBD, the code including instructions to apply a statistical process to a data set indicating the presence or level of at least one marker selected from the group consisting of an anti-neutrophil antibody, anti-*Saccharomyces cerevisiae* antibody, antimicrobial antibody, and combinations thereof in the sample to produce a statistically derived decision classifying the sample as a CD sample, UC sample, or non-IBD sample based upon the presence or level of the at least one marker.

In a further aspect, the present invention provides a system for classifying whether a sample from an individual is associated with IBD, the system comprising:

(a) a data acquisition module configured to produce a data set indicating the presence or level of at least one marker selected from the group consisting of an anti-neutrophil antibody, anti-*Saccharomyces cerevisiae* antibody, antimicrobial antibody, and combinations thereof in the sample;

(b) a data processing module configured to process the data set by applying a statistical process to the data set to produce a statistically derived decision classifying the sample as an IBD sample or non-IBD sample based upon the presence or level of the at least one marker; and (c) a display module configured to display the statistically derived decision.

In a related aspect, the present invention provides a system for classifying whether a sample from an individual is associated with a clinical subtype of IBD, the system comprising:

(a) a data acquisition module configured to produce a data set indicating the presence or level of at least one marker selected from the group consisting of an anti-neutrophil antibody, anti-*Saccharomyces cerevisiae* antibody, antimicrobial antibody, and combinations thereof in the sample;

(b) a data processing module configured to process the data set by applying a statistical process to the data set to produce a statistically derived decision classifying the sample as a CD sample, UC sample, or non-IBD sample based upon the presence or level of the at least one marker; and (c) a display module configured to display the statistically derived decision.

Other objects, features, and advantages of the present invention will be apparent to one of skill in the art from the following detailed description and figures.

BRIEF DESCRIPTION OF THE DRAWINGS

FIG. 4 shows marker input variables, output dependent variables (Diagnosis and Non-IBD/IBD), and probabilities from a C&RT model used as input variables for a neural network model.

DETAILED DESCRIPTION OF THE INVENTION

I. Introduction

Figure 1:
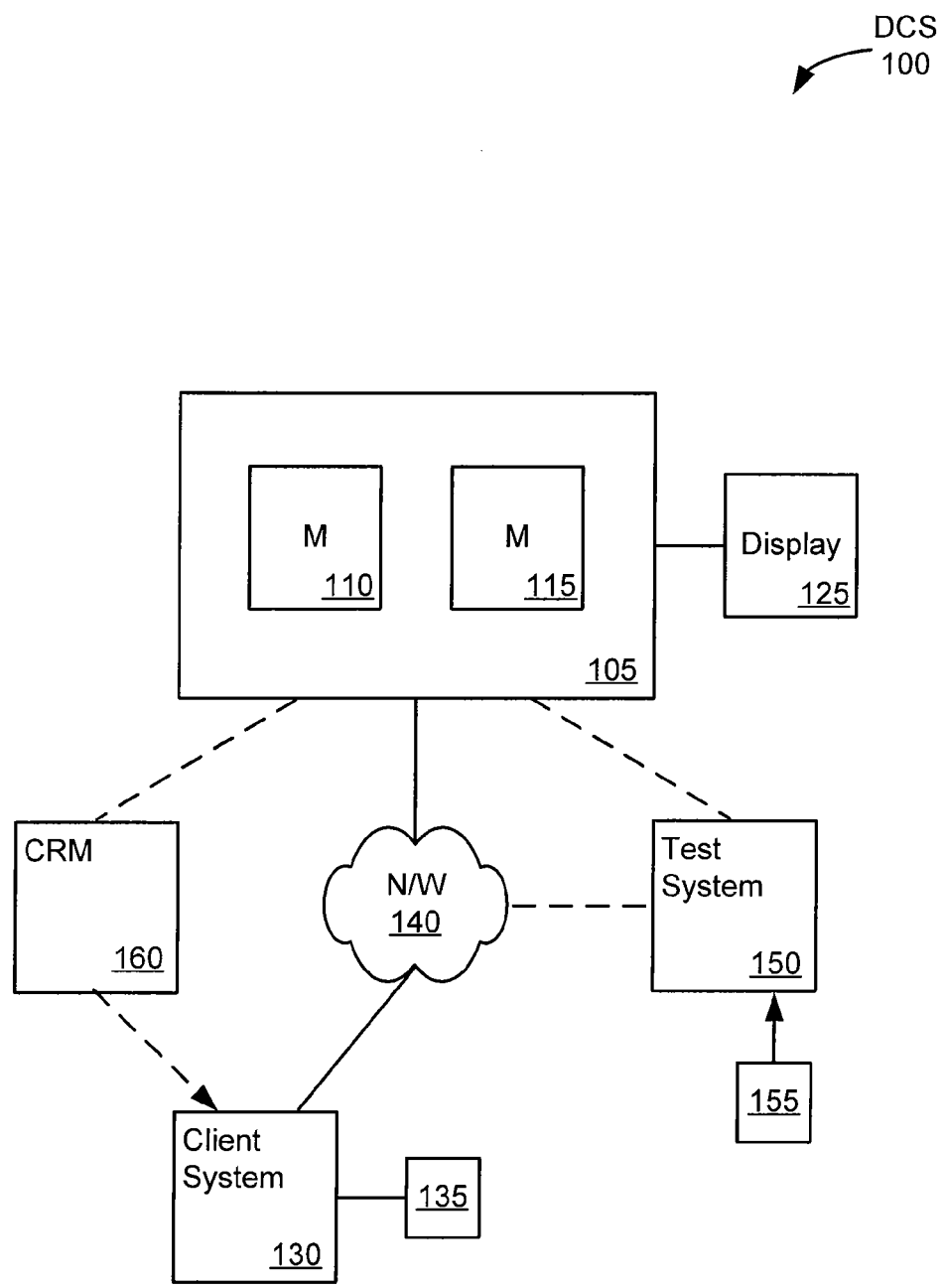
FIG. 1 illustrates a disease classification system (DCS) according to one embodiment of the present invention.

Diagnosing a patient as having inflammatory bowel disease (IBD) can be challenging due to the similarity in symptoms between IBD and other diseases or disorders. For example, patients who have irritable bowel syndrome (IBS), but who exhibit mild signs and symptoms such as bloating, diarrhea, constipation, and abdominal pain can be difficult to distinguish from patients with IBD. As a result, the similarity in symptoms between IBD and IBS renders rapid and accurate diagnosis difficult and hampers early and effective treatment of the disease.

The present invention is based, in part, upon the surprising discovery that the accuracy of classifying a biological sample from an individual as an IBD (e.g., CD or UC) sample can be substantially improved by detecting the presence or level of certain diagnostic markers such as anti-neutrophil antibodies (e.g., ANCA, pANCA, etc.), anti-*Saccharomyces cerevisiae* antibodies (e.g., ASCA-IgA, ASCA-IgG, etc.), and/or antimicrobial antibodies (e.g., anti-OmpC antibodies, anti-flagellin antibodies, anti-I2 antibodies, etc.). In some aspects, the present invention uses statistical algorithms to aid in the classification of a sample as an IBD sample or non-IBD sample. In other aspects, the present invention uses statistical algorithms to aid in the classification of a sample as a CD sample, UC sample, or non-IBD sample. In certain instances, the statistical algorithms described herein can be used to differentiate a CD sample from a UC sample in an individual previously identified as having IBD. Alternatively, the statistical algorithms described herein can be used to determine whether a sample from an individual not previously diagnosed with IBD is a CD sample, UC sample, or non-IBD sample.

Importantly, the present invention illustrates that a diagnostic prediction of IBD or a clinical subtype thereof (e.g., CD or UC) using a combination of learning statistical classifier systems based upon the presence or level of a panel of diagnostic markers is far superior to non-algorithmic techniques such as cut-off value analysis. In fact, a diagnosis of IBD can be made with substantially greater sensitivity, negative predictive value, and/or overall accuracy and the presence of IBD can be detected at an earlier stage of disease progression. In addition, the present invention is useful for differentiating between clinical subtypes of IBD (e.g., CD or UC) with a high degree of overall accuracy. As a result, the stratification of IBD in a particular individual is achieved in a highly accurate manner.

II. Definitions

As used herein, the following terms have the meanings ascribed to them unless specified otherwise.

The term "classifying" includes "to associate" or "to categorize" a sample with a disease state. In certain instances, "classifying" is based on statistical evidence, empirical evidence, or both. In certain embodiments, the methods and systems of classifying use a so-called training set of samples having known disease states. Once established, the training data set serves as a basis, model, or template against which the features of an unknown sample are compared, in order to classify the unknown disease state of the sample. In certain instances, classifying the sample is akin to diagnosing the disease state of the sample. In certain other instances, classifying the sample is akin to differentiating the disease state of the sample from another disease state.

The term "inflammatory bowel disease" or "IBD" refers to gastrointestinal disorders including, without limitation, Crohn's disease (CD), ulcerative colitis (UC), and indeterminate colitis (IC). Inflammatory bowel diseases such as CD, UC, and IC are distinguished from all other disorders, syndromes, and abnormalities of the gastroenterological tract, including irritable bowel syndrome (IBS).

The term "sample" includes any biological specimen obtained from an individual. Suitable samples for use in the present invention include, without limitation, whole blood, plasma, serum, saliva, urine, stool, tears, any other bodily fluid, tissue samples (e.g., biopsy), and cellular extracts thereof (e.g., red blood cellular extract). In a preferred embodiment, the sample is a serum sample. The use of samples such as serum, saliva, and urine is well known in the art (see, e.g., Hashida et al., *J. Clin. Lab. Anal.,* 11:267-86 (1997)). One skilled in the art will appreciate that samples such as serum samples can be diluted prior to the analysis of marker levels.

The term "marker" includes any biochemical marker, serological marker, genetic marker, or other clinical or echographic characteristic that can be used to classify a sample from an individual as an IBD (e.g., CD or UC) sample. Non-limiting examples of markers suitable for use in the present invention are described below and include anti-neutrophil antibodies (e.g., ANCA, pANCA, cANCA, NSNA, SAPPA, etc.), anti-*Saccharomyces cerevisiae* antibodies (e.g., ASCA-IgA, ASCA-IgG, ASCA-IgM, etc.), antimicrobial antibodies (e.g., anti-OmpC antibodies, anti-flagellin antibodies, anti-I2 antibodies, etc.), lactoferrin, anti-lactoferrin antibodies, elastase, C-reactive protein (CRP), calprotectin, hemoglobin, NOD2/CARD15, and combinations thereof. One skilled in the art will know of additional markers suitable for use in the present invention.

The term "individual," "subject," or "patient" typically refers to humans, but also to other animals including, e.g., other primates, rodents, canines, felines, equines, ovines, porcines, and the like.

As used herein, the term "substantially the same amino acid sequence" includes an amino acid sequence that is similar, but not identical to, the naturally-occurring amino acid sequence. For example, an amino acid sequence, i.e., polypeptide, that has substantially the same amino acid sequence as an I2 protein can have one or more modifications such as amino acid additions, deletions, or substitutions relative to the amino acid sequence of the naturally-occurring I2 protein, provided that the modified polypeptide retains substantially at least one biological activity of I2 such as immunoreactivity. Comparison for substantial similarity between amino acid sequences is usually performed with sequences between about 6 and 100 residues, preferably between about 10 and 100 residues, and more preferably between about 25 and 35 residues. A particularly useful modification of a polypeptide of the present invention, or a fragment thereof, is a modification that confers, for example, increased stability. Incorporation of one or more D-amino acids is a modification useful in increasing stability of a polypeptide or polypeptide fragment. Similarly, deletion or substitution of lysine residues can increase stability by protecting the polypeptide or polypeptide fragment against degradation.

The term "clinical factor" includes a symptom in an individual that is associated with IBD. Examples of clinical factors include, without limitation, diarrhea, abdominal pain, cramping, fever, anemia, weight loss, anxiety, depression, and combinations thereof. In some embodiments, a diagnosis of IBD is based upon a combination of analyzing the presence or level of one or more markers in an individual using statistical algorithms and determining whether the individual has one or more clinical factors.

The term "prognosis" includes a prediction of the probable course and outcome of IBD or the likelihood of recovery from the disease. In some embodiments, the use of statistical algorithms provides a prognosis of IBD in an individual. For example, the prognosis can be surgery, development of a clinical subtype of IBD (e.g., CD or UC), development of one or more clinical factors, development of intestinal cancer, or recovery from the disease.

The term "diagnosing IBD" includes the use of the methods, systems, and code of the present invention to determine the presence or absence of IBD in an individual. The term also includes methods, systems, and code for assessing the level of disease activity in an individual. In some embodiments, statistical algorithms are used to diagnose a mild, moderate, severe, or fulminant form of IBD based upon the criteria developed by Truelove et al., *Br. Med. J,* 12:1041-1048 (1955). In other embodiments, statistical algorithms are used to diagnose a mild to moderate, moderate to severe, or severe to fulminant form of IBD based upon the criteria developed by Hanauer et al., *Am. J. Gastroenterol.,* 92:559-566 (1997). One skilled in the art will know of other methods for evaluating the severity of IBD in an individual.

The term "monitoring the progression or regression of IBD" includes the use of the methods, systems, and code of the present invention to determine the disease state (e.g., presence or severity of IBD) of an individual. In certain instances, the results of a statistical algorithm (e.g., a learning statistical classifier system) are compared to those results obtained for the same individual at an earlier time. In some aspects, the methods, systems, and code of the present invention can also be used to predict the progression of IBD, e.g., by determining a likelihood for IBD to progress either rapidly or slowly in an individual based on the presence or level of at least one marker in a sample. In other aspects, the methods, systems, and code of the present invention can also be used to predict the regression of IBD, e.g., by determining a likelihood for IBD to regress either rapidly or slowly in an individual based on the presence or level of at least one marker in a sample.

The term "monitoring drug efficacy in an individual receiving a drug useful for treating IBD" includes the use of the methods, systems, and code of the present invention to determine the disease state (e.g., presence or severity of IBD) of an individual after a therapeutic agent for treating IBD has been administered. In certain instances, the results of a statistical algorithm (e.g., a learning statistical classifier system) are compared to those results obtained for the same individual before initiation of use of the therapeutic agent or at an earlier time in therapy. As used herein, a drug useful for treating IBD is any compound or drug used to improve the health of the individual and includes, without limitation, IBD drugs such as aminosalicylates (e.g., mesalazine, sulfasalazine, and the like), corticosteroids (e.g., prednisone), thiopurines (e.g., azathioprine, 6-mercaptopurine, and the like), methotrexate, monoclonal antibodies (e.g., infliximab), free bases thereof, pharmaceutically acceptable salts thereof, derivatives thereof, analogs thereof, and combinations thereof.

The term "optimizing therapy in an individual having IBD" includes the use of the methods, systems, and code of the present invention to determine the course of therapy for an individual before a therapeutic agent (e.g., IBD drug) has been administered or to adjust the course of therapy for an individual after a therapeutic agent has been administered in order to optimize the therapeutic efficacy of the therapeutic agent. In certain instances, the results of a statistical algorithm (e.g., a learning statistical classifier system) are compared to those results obtained for the same individual at an earlier time during the course of therapy. As such, a comparison of the results provides an indication for the need to change the course of therapy or an indication for the need to increase or decrease the dose of the current course of therapy.

The term "course of therapy" includes any therapeutic approach taken to relieve or prevent one or more symptoms (i.e., clinical factors) associated with IBD. The term encompasses administering any compound, drug, procedure, or regimen useful for improving the health of an individual with IBD and includes any of the therapeutic agents (e.g., IBD drugs) described above as well as surgery. One skilled in the art will appreciate that either the course of therapy or the dose of the current course of therapy can be changed, e.g., based upon the results of a statistical algorithm (e.g., a learning statistical classifier system) obtained using the methods, systems, and code of the present invention.

The term "therapeutically effective amount or dose" includes a dose of a drug that is capable of achieving a therapeutic effect in a subject in need thereof. For example, a therapeutically effective amount of a drug useful for treating IBD can be the amount that is capable of preventing or relieving one or more symptoms associated with IBD. The exact amount can be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

III. Description of the Embodiments

The present invention provides methods, systems, and code for accurately classifying whether a sample from an individual is associated with IBD or a clinical subtype thereof. In some embodiments, the present invention is useful for classifying a sample from an individual as an IBD sample using a statistical algorithm (e.g., a learning statistical classifier system) and/or empirical data (e.g., the presence or level of an IBD marker). The present invention is also useful for differentiating between CD and UC using a statistical algorithm (e.g., a learning statistical classifier system) and/or empirical data (e.g., the presence or level of an IBD marker). Accordingly, the present invention provides an accurate diagnostic prediction of IBD or a clinical subtype thereof and prognostic information useful for guiding treatment decisions.

In one aspect, the present invention provides a method for classifying whether a sample from an individual is associated with IBD, the method comprising:
(a) determining the presence or level of at least one marker selected from the group consisting of an anti-neutrophil antibody, anti-*Saccharomyces cerevisiae* antibody, anti-microbial antibody, and combinations thereof in the sample; and
(b) classifying the sample as an IBD sample or non-IBD sample using a statistical algorithm based upon the presence or level of the at least one marker.

In a related aspect, the present invention provides a method for classifying whether a sample from an individual is associated with a clinical subtype of IBD, the method comprising:
(a) determining the presence or level of at least one marker selected from the group consisting of an anti-neutrophil antibody, anti-*Saccharomyces cerevisiae* antibody, antimicrobial antibody, and combinations thereof in the sample; and
(b) classifying the sample as a CD sample, UC sample, or non-IBD sample using a statistical algorithm based upon the presence or level of the at least one marker.

In some embodiments, the presence or level of at least two, three, four, five, six, seven, eight, nine, ten, or more IBD markers are determined in the individual's sample. In certain instances, the anti-neutrophil antibody comprises an anti-neutrophil cytoplasmic antibody (ANCA), perinuclear anti-neutrophil cytoplasmic antibody (pANCA), cytoplasmic anti-neutrophil cytoplasmic antibody (cANCA), neutrophil-specific nuclear antibody (NSNA), speckling anti-pan polymorphonuclear antibody (SAPPA), and combinations thereof. Preferably, the presence or level of ANCA and/or pANCA is determined in the individual's sample. In certain other instances, the anti-*Saccharomyces cerevisiae* antibody comprises anti-*Saccharomyces cerevisiae* immunoglobulin A (ASCA-IgA), anti-*Saccharomyces cerevisiae* immunoglobulin G (ASCA-IgG), anti-*Saccharomyces cerevisiae* immunoglobulin M (ASCA-IgM), and combinations thereof. Preferably, the presence or level of ASCA-IgA and/or ASCA-IgG is determined in the individual's sample. In further instances, the antimicrobial antibody comprises an anti-outer membrane protein C (anti-OmpC) antibody, anti-flagellin antibody, anti-I2 antibody, and combinations thereof. Preferably, the presence or level of an anti-OmpC antibody and/or anti-flagellin antibody is determined in the individual's sample.

In other embodiments, the at least one marker further comprises one, two, three, four, five, six, seven, eight, nine, ten, or more IBD markers in addition to anti-neutrophil antibodies, anti-*Saccharomyces cerevisiae* antibodies, and/or antimicrobial antibodies. Examples of such IBD markers include, but are not limited to, lactoferrin, anti-lactoferrin antibodies, elastase, C-reactive protein (CRP), calprotectin, hemoglobin, NOD2/CARD15, and combinations thereof.

The sample used for detecting or determining the presence or level of at least one marker is typically whole blood, plasma, serum, saliva, urine, stool (i.e., feces), tears, and any other bodily fluid, or a tissue sample (i.e., biopsy) such as a small intestine or colon sample. Preferably, the sample is serum, whole blood, plasma, stool, urine, or a tissue biopsy. In certain instances, the method of the present invention further comprises obtaining the sample from the individual prior to detecting or determining the presence or level of at least one marker in the sample.

In preferred embodiments, the method of the present invention comprises determining the presence or level of ANCA, ASCA-IgA, ASCA-IgG, anti-OmpC antibody, anti-flagellin antibody, and pANCA in a sample such as serum, plasma, whole blood, or stool. A panel consisting of one or more of the IBD markers described above may be constructed and used for classifying the sample as an IBD (e.g., CD or UC) sample or as a non-IBD sample.

In certain instances, the presence or level of at least one marker is determined using an immunoassay or an immunohistochemical assay. A non-limiting example of an immunoassay suitable for use in the method of the present invention includes an enzyme-linked immunosorbent assay (ELISA). Examples of immunohistochemical assays suitable for use in the method of the present invention include, but are not limited to, immunofluorescence assays such as direct fluorescent antibody assays, indirect fluorescent antibody (IFA) assays, anticomplement immunofluorescence assays, and avidin-biotin immunofluorescence assays. Other types of immunohistochemical assays include immunoperoxidase assays.

In some embodiments, the statistical algorithm used to classify the sample is a learning statistical classifier system. The learning statistical classifier system can be selected from the group consisting of a classification and regression tree (C&RT), random forest (RF), boosted tree, neural network (NN), support vector machine, general chi-squared automatic interaction detector model, interactive tree, multiadaptive regression spline, machine learning classifier, and combinations thereof. Preferably, the learning statistical classifier system is a tree-based statistical algorithm (e.g., C&RT, RF, etc.) and/or a NN (e.g., artificial NN, etc.).

In certain instances, the statistical algorithm is a single learning statistical classifier system. Preferably, the single learning statistical classifier system comprises a tree-based statistical algorithm such as a C&RT or RF. As a non-limiting example, a single learning statistical classifier system can be used to classify the sample as an IBD (e.g., CD or UC) sample or non-IBD sample based upon a prediction or probability value and the presence or level of the at least one IBD marker. The use of a single learning statistical classifier system typically classifies the sample as an IBD (e.g., CD or UC) sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

In certain other instances, the statistical algorithm is a combination of at least two learning statistical classifier systems. Preferably, the combination of learning statistical classifier systems comprises a C&RT or RF and a NN, e.g., used in tandem or parallel. As a non-limiting example, a C&RT can first be used to generate a prediction or probability value based upon the presence or level of at least one IBD marker, and a NN can then be used to classify the sample as an IBD (e.g., CD or UC) sample or non-IBD sample based upon the prediction or probability value and the presence or level of the at least one IBD marker. Advantageously, the hybrid C&RT/NN learning statistical classifier system of the present invention classifies the sample as an IBD (e.g., CD or UC) sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

In some instances, the data obtained from using the learning statistical classifier system or systems can be processed using a processing algorithm. Such a processing algorithm can be selected, for example, from the group consisting of a multilayer perceptron, backpropagation network, and Levenberg-Marquardt algorithm. In other instances, a combination of such processing algorithms can be used, such as in a parallel or serial fashion.

In certain embodiments, the method of the present invention further comprises sending the IBD classification results to a clinician, e.g., a gastroenterologist or a general practitioner. In another embodiment, the method of the present invention further provides a diagnosis in the form of a probability that the individual has IBD or a clinical subtype thereof. For example, the individual can have about a 0%, 5%, 10%, 15%, 20%, 25%, 30%, 35%, 40%, 45%, 50%, 55%, 60%, 65%, 70%, 75%, 80%, 85%, 90%, 95%, or greater probability of having IBD or a clinical subtype thereof. In yet another embodiment, the method of the present invention further provides a prognosis of IBD in the individual. For example, the prognosis can be surgery, development of a clinical subtype of IBD (e.g., CD or UC), development of one or more symptoms, development of intestinal cancer, or recovery from the disease. In some instances, the method of classifying a sample as an IBD sample is further based on the symptoms (i.e., clinical factors) of the individual from which the sample is obtained. The symptoms or group of symptoms can be, for example, diarrhea, abdominal pain, cramping, fever, anemia, weight loss, anxiety, depression, and combinations thereof.

In some embodiments, the diagnosis of an individual as having IBD or a clinical subtype thereof is followed by administering to the individual a therapeutically effective amount of a drug useful for treating one or more symptoms associated with IBD or the IBD subtype (e.g., CD or UC). Suitable IBD drugs include, but are not limited to, aminosalicylates (e.g., mesalazine, sulfasalazine, and the like), corticosteroids (e.g., prednisone), thiopurines (e.g., azathioprine, 6-mercaptopurine, and the like), methotrexate, monoclonal antibodies (e.g., infliximab), free bases thereof, pharmaceutically acceptable salts thereof, derivatives thereof, analogs thereof, and combinations thereof.

In certain instances, the statistical algorithms of the present invention can be used to differentiate a CD sample from a UC sample in an individual previously identified as having IBD. In certain other instances, the statistical algorithms of the present invention can be used to classify a sample from an individual not previously diagnosed with IBD as a CD sample, UC sample, or non-IBD sample.

In another aspect, the present invention provides a method for monitoring the progression or regression of IBD in an individual, the method comprising:
  (a) determining the presence or level of at least one marker selected from the group consisting of an anti-neutrophil antibody, anti-*Saccharomyces cerevisiae* antibody, antimicrobial antibody, and combinations thereof in a sample from the individual; and
  (b) determining the presence or severity of IBD in the individual using a statistical algorithm based upon the presence or level of the at least one marker.

In a related aspect, the present invention provides a method for monitoring drug efficacy in an individual receiving a drug useful for treating IBD, the method comprising:
  (a) determining the presence or level of at least one marker selected from the group consisting of an anti-neutrophil antibody, anti-*Saccharomyces cerevisiae* antibody, antimicrobial antibody, and combinations thereof in a sample from the individual; and
  (b) determining the presence or severity of IBD in the individual using a statistical algorithm based upon the presence or level of the at least one marker.

As described above, the present invention typically involves determining the presence or level of at least one, two, three, four, five, six, seven, eight, nine, ten, or more IBD markers in the individual's sample. In certain instances, the anti-neutrophil antibody comprises ANCA, pANCA, cANCA, NSNA, SAPPA, and combinations thereof. Preferably, the presence or level of ANCA and/or pANCA is determined in the individual's sample. In certain other instances, the anti-*Saccharomyces cerevisiae* antibody comprises ASCA-IgA, ASCA-IgG, ASCA-IgM, and combinations thereof. Preferably, the presence or level of ASCA-IgA and/or ASCA-IgG is determined in the individual's sample. In further instances, the antimicrobial antibody comprises an anti-OmpC antibody, anti-flagellin antibody, anti-I2 antibody, and combinations thereof. Preferably, the presence or level of an anti-OmpC antibody and/or anti-flagellin antibody is determined in the individual's sample.

In addition to anti-neutrophil antibodies, anti-*Saccharomyces cerevisiae* antibodies, and/or antimicrobial antibodies, the at least one marker can further comprise one, two, three, four, five, six, seven, eight, nine, ten, or more IBD markers such as, for example, lactoferrin, anti-lactoferrin antibodies, elastase, C-reactive protein (CRP), calprotectin, hemoglobin, NOD2/CARD15, and combinations thereof.

The sample used for detecting or determining the presence or level of at least one marker is typically whole blood, plasma, serum, saliva, urine, stool (i.e., feces), tears, and any other bodily fluid, or a tissue sample (i.e., biopsy) such as a small intestine or colon sample. Preferably, the sample is serum, whole blood, plasma, stool, urine, or a tissue biopsy. In certain instances, the method of the present invention further comprises obtaining the sample from the individual prior to detecting or determining the presence or level of at least one marker in the sample.

In preferred embodiments, the method of the present invention comprises determining the presence or level of ANCA, ASCA-IgA, ASCA-IgG, anti-OmpC antibody, anti-flagellin antibody, and pANCA in a sample such as serum, plasma, whole blood, or stool. A panel consisting of one or more of the IBD markers described above may be constructed and used for determining the presence or severity of IBD (e.g., CD or UC) in the individual.

In certain instances, the presence or level of at least one marker is determined using an immunoassay or an immunohistochemical assay. A non-limiting example of an immunoassay suitable for use in the method of the present invention includes an ELISA. Examples of immunohistochemical assays suitable for use in the method of the present invention include, but are not limited to, immunofluorescence assays such as direct fluorescent antibody assays, IFA assays, anti-complement immunofluorescence assays, and avidin-biotin immunofluorescence assays. Other types of immunohistochemical assays include immunoperoxidase assays.

In some embodiments, the statistical algorithm used to determine the presence or severity of IBD is a learning statistical classifier system. The learning statistical classifier system can be selected from the group consisting of a classification and regression tree (C&RT), random forest (RF), boosted tree, neural network (NN), support vector machine, general chi-squared automatic interaction detector model, interactive tree, multiadaptive regression spline, machine learning classifier, and combinations thereof. Preferably, the learning statistical classifier system is a tree-based statistical algorithm (e.g., C&RT, random forest, etc.) and/or a NN (e.g., artificial NN, etc.).

In certain instances, the statistical algorithm is a single learning statistical classifier system. Preferably, the single learning statistical classifier system is a tree-based statistical algorithm (e.g., C&RT, RF, etc.). In certain other instances, the statistical algorithm is a combination of at least two learning statistical classifier systems. Preferably, the combination of learning statistical classifier systems comprises a C&RT or RF and a NN, e.g., used in tandem or parallel. As a non-limiting example, a C&RT can first be used to generate a prediction or probability value based upon the presence or level of at least one IBD marker, and a NN can then be used to determine the presence or severity of IBD in the individual based upon the prediction or probability value and the presence or level of the at least one IBD marker.

In some instances, the data obtained from using the learning statistical classifier system or systems can be processed using a processing algorithm. Such a processing algorithm can be selected, for example, from the group consisting of a multilayer perceptron, backpropagation network, and Levenberg-Marquardt algorithm. In other instances, a combination of such processing algorithms can be used, such as in a parallel or serial fashion.

In certain embodiments, the method of the present invention can further comprise comparing the presence or severity of IBD determined in step (b) to the presence or severity of IBD in the individual at an earlier time. As a non-limiting example, the presence or severity of IBD determined for an individual receiving a therapeutic agent useful for treating IBD can be compared to the presence or severity of IBD determined for the same individual before initiation of use of the therapeutic agent or at an earlier time in therapy. In certain other embodiments, the method can further comprise sending the IBD monitoring results to a clinician, e.g., a gastroenterologist or a general practitioner.

In yet another aspect, the present invention provides a computer-readable medium including code for controlling one or more processors to classify whether a sample from an individual is associated with IBD, the code including instructions to apply a statistical process to a data set indicating the presence or level of at least one marker selected from the group consisting of an anti-neutrophil antibody, anti-*Saccharomyces cerevisiae* antibody, antimicrobial antibody, and combinations thereof in the sample to produce a statistically derived decision classifying the sample as an IBD sample or non-IBD sample based upon the presence or level of the at least one marker.

In a related aspect, the present invention provides a computer-readable medium including code for controlling one or more processors to classify whether a sample from an individual is associated with a clinical subtype of IBD, the code including instructions to apply a statistical process to a data set indicating the presence or level of at least one marker selected from the group consisting of an anti-neutrophil antibody, anti-*Saccharomyces cerevisiae* antibody, antimicrobial antibody, and combinations thereof in the sample to produce a statistically derived decision classifying the sample as a CD sample, UC sample, or non-IBD sample based upon the presence or level of the at least one marker.

In one embodiment, the statistical process is a learning statistical classifier system. Examples of learning statistical classifier systems suitable for use in the present invention are described above. In certain instances, the statistical process is a single learning statistical classifier system such as, for example, a C&RT or RF. In certain other instances, the statistical process is a combination of at least two learning statistical classifier systems. As a non-limiting example, the combination of learning statistical classifier systems comprises a C&RT or RF and a NN, e.g., used in tandem. In some instances, the data obtained from using the learning statistical classifier system or systems can be processed using a processing algorithm.

In a further aspect, the present invention provides a system for classifying whether a sample from an individual is associated with IBD, the system comprising:
  (a) a data acquisition module configured to produce a data set indicating the presence or level of at least one marker selected from the group consisting of an anti-neutrophil antibody, anti-*Saccharomyces cerevisiae* antibody, antimicrobial antibody, and combinations thereof in the sample;
  (b) a data processing module configured to process the data set by applying a statistical process to the data set to produce a statistically derived decision classifying the sample as an IBD sample or non-IBD sample based upon the presence or level of the at least one marker; and (c) a display module configured to display the statistically derived decision.

In a related aspect, the present invention provides a system for classifying whether a sample from an individual is associated with a clinical subtype of IBD, the system comprising:

(a) a data acquisition module configured to produce a data set indicating the presence or level of at least one marker selected from the group consisting of an anti-neutrophil antibody, anti-*Saccharomyces cerevisiae* antibody, anti-microbial antibody, and combinations thereof in the sample;

(b) a data processing module configured to process the data set by applying a statistical process to the data set to produce a statistically derived decision classifying the sample as a CD sample, UC sample, or non-IBD sample based upon the presence or level of the at least one marker; and (c) a display module configured to display the statistically derived decision.

In one embodiment, the statistical process is a learning statistical classifier system. Examples of learning statistical classifier systems suitable for use in the present invention are described above. In certain instances, the statistical process is a single learning statistical classifier system. In certain other instances, the statistical process is a combination of at least two learning statistical classifier systems. In some instances, the data obtained from using the learning statistical classifier system or systems can be processed using a processing algorithm.

IV. Clinical Subtypes of IBD

Crohn's disease (CD) is a disease of chronic inflammation that can involve any part of the gastrointestinal tract. Commonly, the distal portion of the small intestine, i.e., the ileum, and the cecum are affected. In other cases, the disease is confined to the small intestine, colon, or anorectal region. CD occasionally involves the duodenum and stomach, and more rarely the esophagus and oral cavity.

The variable clinical manifestations of CD are, in part, a result of the varying anatomic localization of the disease. The most frequent symptoms of CD are abdominal pain, diarrhea, and recurrent fever. CD is commonly associated with intestinal obstruction or fistula, an abnormal passage between diseased loops of bowel. CD also includes complications such as inflammation of the eye, joints, and skin, liver disease, kidney stones, and amyloidosis. In addition, CD is associated with an increased risk of intestinal cancer.

Several features are characteristic of the pathology of CD. The inflammation associated with CD, known as transmural inflammation, involves all layers of the bowel wall. Thickening and edema, for example, typically also appear throughout the bowel wall, with fibrosis present in long-standing forms of the disease. The inflammation characteristic of CD is discontinuous in that segments of inflamed tissue, known as "skip lesions," are separated by apparently normal intestine. Furthermore, linear ulcerations, edema, and inflammation of the intervening tissue lead to a "cobblestone" appearance of the intestinal mucosa, which is distinctive of CD.

A hallmark of CD is the presence of discrete aggregations of inflammatory cells, known as granulomas, which are generally found in the submucosa. Some CD cases display typical discrete granulomas, while others show a diffuse granulomatous reaction or a nonspecific transmural inflammation. As a result, the presence of discrete granulomas is indicative of CD, although the absence of granulomas is also consistent with the disease. Thus, transmural or discontinuous inflammation, rather than the presence of granulomas, is a preferred diagnostic indicator of CD (Rubin and Farber, Pathology (Second Edition), Philadelphia, J.B. Lippincott Company (1994)).

Ulcerative colitis (UC) is a disease of the large intestine characterized by chronic diarrhea with cramping, abdominal pain, rectal bleeding, loose discharges of blood, pus, and mucus. The manifestations of UC vary widely. A pattern of exacerbations and remissions typifies the clinical course for about 70% of UC patients, although continuous symptoms without remission are present in some patients with UC. Local and systemic complications of UC include arthritis, eye inflammation such as uveitis, skin ulcers, and liver disease. In addition, UC, and especially the long-standing, extensive form of the disease is associated with an increased risk of colon carcinoma.

UC is a diffuse disease that usually extends from the most distal part of the rectum for a variable distance proximally. The term "left-sided colitis" describes an inflammation that involves the distal portion of the colon, extending as far as the splenic flexure. Sparing of the rectum or involvement of the right side (proximal portion) of the colon alone is unusual in UC. The inflammatory process of UC is limited to the colon and does not involve, for example, the small intestine, stomach, or esophagus. In addition, UC is distinguished by a superficial inflammation of the mucosa that generally spares the deeper layers of the bowel wall. Crypt abscesses, in which degenerated intestinal crypts are filled with neutrophils, are also typical of UC (Rubin and Farber, supra).

In comparison with CD, which is a patchy disease with frequent sparing of the rectum, UC is characterized by a continuous inflammation of the colon that usually is more severe distally than proximally. The inflammation in UC is superficial in that it is usually limited to the mucosal layer and is characterized by an acute inflammatory infiltrate with neutrophils and crypt abscesses. In contrast, CD affects the entire thickness of the bowel wall with granulomas often, although not always, present. Disease that terminates at the ileocecal valve, or in the colon distal to it, is indicative of UC, while involvement of the terminal ileum, a cobblestone-like appearance, discrete ulcers, or fistulas suggests CD.

Indeterminate colitis (IC) is a clinical subtype of IBD that includes both features of CD and UC. Such an overlap in the symptoms of both diseases can occur temporarily (e.g., in the early stages of the disease) or persistently (e.g., throughout the progression of the disease) in patients with IC. Clinically, IC is characterized by abdominal pain and diarrhea with or without rectal bleeding. For example, colitis with intermittent multiple ulcerations separated by normal mucosa is found in patients with the disease. Histologically, there is a pattern of severe ulceration with transmural inflammation. The rectum is typically free of the disease and the lymphoid inflammatory cells do not show aggregation. Although deep slit-like fissures are observed with foci of myocytolysis, the intervening mucosa is typically minimally congested with the preservation of goblet cells in patients with IC.

V. IBD Markers

A variety of inflammatory bowel disease (IBD) markers, such as biochemical markers, serological markers, genetic markers, or other clinical or echographic characteristics, are suitable for use in the statistical algorithms of the present invention for ruling in IBD, e.g., by classifying a sample from an individual as an IBD sample. The IBD markers described herein are also suitable for use in the statistical algorithms of the present invention for differentiating between clinical subtypes of IBD, e.g., by classifying a sample from an individual as a CD or UC sample. Examples of markers suitable for use in the present invention include, but are not limited to, anti-neutrophil antibodies (e.g., ANCA, pANCA, cANCA, NSNA, SAPPA, etc.), anti-*Saccharomyces cerevisiae* antibodies (e.g., ASCA-IgA, ASCA-IgG, ASCA-IgM, etc.), anti-microbial antibodies (e.g., anti-OmpC antibodies, anti-flagellin antibodies, anti-I2 antibodies, etc.), lactoferrin, anti-lactoferrin antibodies, elastase, C-reactive protein (CRP), calprotectin, hemoglobin, NOD2/CARD 15, and combinations thereof. One skilled in the art will know of additional markers suitable for use in the statistical algorithms of the present invention.

The determination of ANCA levels and/or the presence or absence of pANCA in a sample is useful in the present invention. As used herein, the term "anti-neutrophil cytoplasmic antibody" or "ANCA" includes antibodies directed to cytoplasmic and/or nuclear components of neutrophils. ANCA activity can be divided into several broad categories based upon the ANCA staining pattern in neutrophils: (1) cytoplasmic neutrophil staining without perinuclear highlighting (cANCA); (2) perinuclear staining around the outside edge of the nucleus (pANCA); (3) perinuclear staining around the inside edge of the nucleus (NSNA); and (4) diffuse staining with speckling across the entire neutrophil (SAPPA). In certain instances, pANCA staining is sensitive to DNase treatment. The term ANCA encompasses all varieties of anti-neutrophil reactivity, including, but not limited to, cANCA, pANCA, NSNA, and SAPPA. Similarly, the term ANCA encompasses all immunoglobulin isotypes including, without limitation, immunoglobulin A and G.

ANCA levels in a sample from an individual can be determined, for example, using an immunoassay such as an enzyme-linked immunosorbent assay (ELISA) with alcohol-fixed neutrophils (see, e.g., Example 1). The presence or absence of a particular category of ANCA such as pANCA can be determined, for example, using an immunohistochemical assay such as an indirect fluorescent antibody (IFA) assay. Preferably, the presence or absence of pANCA in a sample is determined using an immunofluorescence assay with DNase-treated, fixed neutrophils (see, e.g., Example 2). In addition to fixed neutrophils, antigens specific for ANCA that are suitable for determining ANCA levels include, without limitation, unpurified or partially purified neutrophil extracts; purified proteins, protein fragments, or synthetic peptides such as histone H1 or ANCA-reactive fragments thereof (see, e.g., U.S. Pat. No. 6,074,835); histone H1-like antigens, porin antigens, *Bacteroides* antigens, or ANCA-reactive fragments thereof (see, e.g., U.S. Pat. No. 6,033,864); secretory vesicle antigens or ANCA-reactive fragments thereof (see, e.g., U.S. patent application Ser. No. 08/804,106); and anti-ANCA idiotypic antibodies. One skilled in the art will appreciate that the use of additional antigens specific for ANCA is within the scope of the present invention.

The determination of ASCA (e.g., ASCA-IgA and/or ASCA-IgG) levels in a sample is also useful in the present invention. As used herein, the term "anti-*Saccharomyces cerevisiae* immunoglobulin A" or "ASCA-IgA" includes antibodies of the immunoglobulin A isotype that react specifically with *S. cerevisiae*. Similarly, the term "anti-*Saccharomyces cerevisiae* immunoglobulin G" or "ASCA-IgG" includes antibodies of the immunoglobulin G isotype that react specifically with *S. cerevisiae*.

The determination of whether a sample is positive for ASCA-IgA or ASCA-IgG is made using an antigen specific for ASCA. Such an antigen can be any antigen or mixture of antigens that is bound specifically by ASCA-IgA and/or ASCA-IgG. Although ASCA antibodies were initially characterized by their ability to bind *S. cerevisiae*, those of skill in the art will understand that an antigen that is bound specifically by ASCA can be obtained from *S. cerevisiae* or from a variety of other sources so long as the antigen is capable of binding specifically to ASCA antibodies. Accordingly, exemplary sources of an antigen specific for ASCA, which can be used to determine the levels of ASCA-IgA and/or ASCA-IgG in a sample, include, without limitation, whole killed yeast cells such as *Saccharomyces* or *Candida* cells; yeast cell wall mannan such as phosphopeptidomannan (PPM); oligosaccharides such as oligomannosides; neoglycolipids; anti-ASCA idiotypic antibodies; and the like. Different species and strains of yeast, such as *S. cerevisiae* strain Su1, Su2, CBS 1315, or BM 156, or *Candida albicans* strain VW32, are suitable for use as an antigen specific for ASCA-IgA and/or ASCA-IgG. Purified and synthetic antigens specific for ASCA are also suitable for use in determining the levels of ASCA-IGA and/or ASCA-IgG in a sample. Examples of purified antigens include, without limitation, purified oligosaccharide antigens such as oligomannosides. Examples of synthetic antigens include, without limitation, synthetic oligomannosides such as those described in U.S. Patent Publication No. 20030105060, e.g., D-Man β(1-2) D-Man β(1-2) D-Man β(1-2) D-Man-OR, D-Man α(1-2) D-Man α(1-2) D-Man α(1-2) D-Man-OR, and D-Man α(1-3) D-Man α(1-2) D-Man α(1-2) D-Man-OR, wherein R is a hydrogen atom, a $C_1$ to $C_{20}$ alkyl, or an optionally labeled connector group.

Preparations of yeast cell wall mannans, e.g., PPM, can be used in determining the levels of ASCA-IGA and/or ASCA-IgG in a sample. Such water-soluble surface antigens can be prepared by any appropriate extraction technique known in the art, including, for example, by autoclaving, or can be obtained commercially (see, e.g., Lindberg et al., *Gut*, 33:909-913 (1992)). The acid-stable fraction of PPM is also useful in the statistical algorithms of the present invention (Sendid et al, *Clin. Diag. Lab. Immunol.*, 3:219-226 (1996)). An exemplary PPM that is useful in determining ASCA levels in a sample is derived from *S. uvarum* strain ATCC #38926. Example 3 describes the preparation of yeast cell well mannan and an analysis of ASCA levels in a sample using an ELISA assay.

Purified oligosaccharide antigens such as oligomannosides can also be useful in determining the levels of ASCA-IgA and/or ASCA-IgG in a sample. The purified oligomannoside antigens are preferably converted into neoglycolipids as described in, for example, Faille et al., *Eur. J. Microbiol. Infect. Dis.*, 11:438-446 (1992). One skilled in the art understands that the reactivity of such an oligomannoside antigen with ASCA can be optimized by varying the mannosyl chain length (Frosh et al., *Proc Natl. Acad. Sci. USA*, 82:1194-1198 (1985)); the anomeric configuration (Fukazawa et al., In "Immunology of Fungal Disease," E. Kurstak (ed.), Marcel Dekker Inc., New York, pp. 37-62 (1989); Nishikawa et al., *Microbiol. Immunol.*, 34:825-840 (1990); Poulain et al., *Eur. J. Clin. Microbiol.*, 23:46-52 (1993); Shibata et al., *Arch. Biochem. Biophys.*, 243:338-348 (1985); Trinel et al., *Infect. Immun.*, 60:3845-3851 (1992)); or the position of the linkage (Kikuchi et al., *Planta*, 190:525-535 (1993)).

Suitable oligomannosides for use in the methods of the present invention include, without limitation, an oligomannoside having the mannotetraose Man(1-3) Man(1-2) Man(1-2) Man. Such an oligomannoside can be purified from PPM as described in, e.g., Faille et al., supra. An exemplary neoglycolipid specific for ASCA can be constructed by releasing the oligomannoside from its respective PPM and subsequently coupling the released oligomannoside to 4-hexadecylaniline or the like.

The determination of anti-OmpC antibody levels in a sample is also useful in the present invention. As used herein, the term "anti-outer membrane protein C antibody" or "anti-OmpC antibody" includes antibodies directed to a bacterial outer membrane porin as described in, e.g., PCT Patent Publication No. WO 01/89361. The term "outer membrane protein C" or "OmpC" includes a bacterial porin that is immunoreactive with an anti-OmpC antibody.

The level of anti-OmpC antibody present in a sample from an individual can be determined using an OmpC protein or a fragment thereof such as an immunoreactive fragment thereof. Suitable OmpC antigens useful in determining anti-OmpC antibody levels in a sample include, without limitation, an OmpC protein, an OmpC polypeptide having substantially the same amino acid sequence as the OmpC protein, or a fragment thereof such as an immunoreactive fragment thereof. As used herein, an OmpC polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with an OmpC protein, with the amino acid identity determined using a sequence alignment program such as CLUSTALW. Such antigens can be prepared, for example, by purification from enteric bacteria such as $E.\ coli$, by recombinant expression of a nucleic acid such as Genbank Accession No. K00541, by synthetic means such as solution or solid phase peptide synthesis, or by using phage display. Example 4 describes the preparation of OmpC protein and an analysis of anti-OmpC antibody levels in a sample using an ELISA assay.

The determination of anti-I2 antibody levels in a sample is also useful in the present invention. As used herein, the term "anti-I2 antibody" includes antibodies directed to a microbial antigen sharing homology to bacterial transcriptional regulators as described in, e.g., U.S. Pat. No. 6,309,643. The term "I2" includes a microbial antigen that is immunoreactive with an anti-I2 antibody. The microbial I2 protein is a polypeptide of 100 amino acids sharing some similarity weak homology with the predicted protein 4 from $C.\ pasteurianum$, Rv3557c from $Mycobacterium\ tuberculosis$, and a transcriptional regulator from $Aquifex\ aeolicus$. The nucleic acid and protein sequences for the I2 protein are described in, e.g., U.S. Pat. No. 6,309,643.

The level of anti-I2 antibody present in a sample from an individual can be determined using an I2 protein or a fragment thereof such as an immunoreactive fragment thereof. Suitable I2 antigens useful in determining anti-I2 antibody levels in a sample include, without limitation, an I2 protein, an I2 polypeptide having substantially the same amino acid sequence as the I2 protein, or a fragment thereof such as an immunoreactive fragment thereof. Such I2 polypeptides exhibit greater sequence similarity to the I2 protein than to the $C.\ pasteurianum$ protein 4 and include isotype variants and homologs thereof. As used herein, an I2 polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a naturally-occurring I2 protein, with the amino acid identity determined using a sequence alignment program such as CLUSTALW. Such I2 antigens can be prepared, for example, by purification from microbes, by recombinant expression of a nucleic acid encoding an I2 antigen, by synthetic means such as solution or solid phase peptide synthesis, or by using phage display. Example 5 describes the preparation of recombinant I2 protein and an analysis of anti-I2 antibody levels in a sample using an ELISA assay or a histological assay.

The determination of anti-flagellin antibody levels in a sample is also useful in the present invention. As used herein, the term "anti-flagellin antibody" includes antibodies directed to a protein component of bacterial flagella as described in, e.g., PCT Patent Publication No. WO 03/053220 and U.S. Patent Publication No. 20040043931. The term "flagellin" includes a bacterial flagellum protein that is immunoreactive with an anti-flagellin antibody. Microbial flagellins are proteins found in bacterial flagellum that arrange themselves in a hollow cylinder to form the filament.

The level of anti-flagellin antibody present in a sample from an individual can be determined using a flagellin protein or a fragment thereof such as an immunoreactive fragment thereof. Suitable flagellin antigens useful in determining anti-flagellin antibody levels in a sample include, without limitation, a flagellin protein such as Cbir-1 flagellin, flagellin X, flagellin A, flagellin B, fragments thereof, and combinations thereof, a flagellin polypeptide having substantially the same amino acid sequence as the flagellin protein, or a fragment thereof such as an immunoreactive fragment thereof. As used herein, a flagellin polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a naturally-occurring flagellin protein, with the amino acid identity determined using a sequence alignment program such as CLUSTALW. Such flagellin antigens can be prepared, e.g., by purification from bacterium such as $Helicobacter\ Bilis$, $Helicobacter\ mustelae$, $Helicobacter\ pylori$, $Butyrivibrio\ fibrisolvens$, and bacterium found in the cecum, by recombinant expression of a nucleic acid encoding a flagellin antigen, by synthetic means such as solution or solid phase peptide synthesis, or by using phage display.

The determination of the presence or level of lactoferrin in a sample is also useful in the present invention. In certain instances, the presence or level of lactoferrin is detected at the level of mRNA expression with an assay such as, for example, a hybridization assay or an amplification-based assay. In certain other instances, the presence or level of lactoferrin is detected at the level of protein expression using, for example, an immunoassay (e.g., ELISA) or an immunohistochemical assay. An ELISA kit available from Calbiochem (San Diego, Calif.) can be used to detect human lactoferrin in a plasma, urine, bronchoalveolar lavage, or cerebrospinal fluid sample. Similarly, an ELISA kit available from U.S. Biological (Swampscott, Mass.) can be used to determine the level of lactoferrin in a plasma sample. Likewise, ELISA kits available from TECHLAB, Inc. (Blacksburg, Va.) can be used to determine the level of lactoferrin in a stool sample. Additionally, U.S. Patent Publication No. 20040137536 describes an ELISA assay for determining the presence of elevated lactoferrin levels in a stool sample, and U.S. Patent Publication No. 20040033537 describes an ELISA assay for determining the concentration of endogenous lactoferrin in a stool, mucus, or bile sample. In some embodiments, then presence or level of anti-lactoferrin antibodies can be detected in a sample using, e.g., lactoferrin protein or a fragment thereof.

The determination of the presence or level of C-reactive protein (CRP) in a sample is also useful in the present invention. In certain instances, the presence or level of CRP is detected at the level of mRNA expression with an assay such as, for example, a hybridization assay or an amplification-based assay. In certain other instances, the presence or level of CRP is detected at the level of protein expression using, for example, an immunoassay (e.g., ELISA) or an immunohistochemical assay. For example, a sandwich colorimetric ELISA assay available from Alpco Diagnostics (Salem, N.H.) can be used to determine the level of CRP in a serum, plasma, urine, or stool sample. Similarly, an ELISA kit available from Biomeda Corporation (Foster City, Calif.) can be used to detect CRP levels in a sample. Other methods for determining CRP levels in a sample are described in, e.g., U.S. Pat. Nos. 6,838,250 and 6,406,862; and U.S. Patent Publication Nos. 20060024682 and 20060019410.

In addition, hemoccult, fecal occult blood, is often indicative of gastrointestinal illness and various kits have been developed to monitor gastrointestinal bleeding. For example, Hemoccult SENSA, a Beckman Coulter product, is a diagnostic aid for gastrointestinal bleeding, iron deficiency, peptic ulcers, ulcerative colitis, and, in some instances, in screening for colorectal cancer. This particular assay is based on the oxidation of guaiac by hydrogen peroxide to produce a blue color. A similar calorimetric assay is commercially available from Helena Laboratories (Beaumont, Tex.) for the detection of blood in stool samples. Other methods for detecting occult blood in a stool sample by determining the presence or level of hemoglobin or heme activity are described in, e.g., U.S. Pat. Nos. 4,277,250, 4,920,045, 5,081,040, and 5,310,684.

Calprotectin is a calcium and zinc-binding protein found in all cells, tissues, and fluids in the body. Calprotectin is a major protein in neutrophilic granulocytes and macrophages and accounts for as much as 60% of the total protein in the cytosolic fraction of these cells. It is therefore a surrogate marker of neutrophil turnover. Its concentration in stool correlates with the intensity of neutrophil infiltration of the intestinal mucosa and with the severity of inflammation. Calprotectin can be measured with an ELISA using small (50-100 mg) fecal samples (see, e.g., Johne et al., *Scand J. Gastroenterol.*, 36:291-296 (2001)).

The determination of the presence of polymorphisms in the NOD2/CARD15 gene in a sample is also useful in the present invention. For example, polymorphisms in the NOD2 gene such as a C2107T nucleotide variant that results in a R703W protein variant can be identified in a sample from an individual (see, e.g., U.S. Patent Publication No. 20030190639). In an alternative embodiment, NOD2 mRNA levels can be used as a diagnostic marker of the present invention to aid in classifying IBD.

VI. Assays

Any of a variety of assays, techniques, and kits known in the art can be used to determine the presence or level of one or more markers in a sample to classify whether the sample is associated with IBD or a clinical subtype thereof.

The present invention relies, in part, on determining the presence or level of at least one marker in a sample obtained from an individual. As used herein, the term "determining the presence of at least one marker" includes determining the presence of each marker of interest by using any quantitative or qualitative assay known to one of skill in the art. In certain instances, qualitative assays that determine the presence or absence of a particular trait, variable, or biochemical or serological substance (e.g., protein or antibody) are suitable for detecting each marker of interest. In certain other instances, quantitative assays that determine the presence or absence of RNA, protein, antibody, or activity are suitable for detecting each marker of interest. As used herein, the term "determining the level of at least one marker" includes determining the level of each marker of interest by using any direct or indirect quantitative assay known to one of skill in the art. In certain instances, quantitative assays that determine, for example, the relative or absolute amount of RNA, protein, antibody, or activity are suitable for determining the level of each marker of interest. One skilled in the art will appreciate that any assay useful for determining the level of a marker is also useful for determining the presence or absence of the marker.

As used herein, the term "antibody" includes a population of immunoglobulin molecules, which can be polyclonal or monoclonal and of any isotype, or an immunologically active fragment of an immunoglobulin molecule. Such an immunologically active fragment contains the heavy and light chain variable regions, which make up the portion of the antibody molecule that specifically binds an antigen. For example, an immunologically active fragment of an immunoglobulin molecule known in the art as Fab, Fab' or F(ab')$_2$ is included within the meaning of the term antibody.

Flow cytometry can be used to determine the presence or level of one or more markers in a sample. Such flow cytometric assays, including bead based immunoassays, can be used to determine, e.g., antibody marker levels in the same manner as described for detecting serum antibodies to *Candida albicans* and HIV proteins (see, e.g., Bishop et al., *J. Immunol. Methods,* 210:79-87 (1997); McHugh et al., *J. Immunol. Methods,* 116:213 (1989); Scillian et al., *Blood,* 73:2041 (1989)).

Phage display technology for expressing a recombinant antigen specific for a marker can also be used to determine the presence or level of one or more markers in a sample. Phage particles expressing an antigen specific for, e.g., an antibody marker can be anchored, if desired, to a multi-well plate using an antibody such as an anti-phage monoclonal antibody (Felici et al., "Phage-Displayed Peptides as Tools for Characterization of Human Sera" in Abelson (Ed.), *Methods in Enzymol.,* 267, San Diego: Academic Press, Inc. (1996)).

A variety of immunoassay techniques, including competitive and non-competitive immunoassays, can be used to determine the presence or level of one or more markers in a sample (see, e.g., Self et al, *Curr. Opin. Biotechnol.,* 7:60-65 (1996)). The term immunoassay encompasses techniques including, without limitation, enzyme immunoassays (EIA) such as enzyme multiplied immunoassay technique (EMIT), enzyme-linked immunosorbent assay (ELISA), antigen capture ELISA, sandwich ELISA, IgM antibody capture ELISA (MAC ELISA), and microparticle enzyme immunoassay (MEIA); capillary electrophoresis immunoassays (CEIA); radioimmunoassays (RIA); immunoradiometric assays (IRMA); fluorescence polarization immunoassays (FPIA); and chemiluminescence assays (CL). If desired, such immunoassays can be automated. Immunoassays can also be used in conjunction with laser induced fluorescence (see, e.g., Schmalzing et al., *Electrophoresis,* 18:2184-2193 (1997); Bao, *J. Chromatogr. B. Biomed. Sci.,* 699:463-480 (1997)). Liposome immunoassays, such as flow-injection liposome immunoassays and liposome immunosensors, are also suitable for use in the present invention (see, e.g., Rongen et al., *J. Immunol. Methods,* 204:105-133 (1997)). In addition, nephelometry assays, in which the formation of protein/antibody complexes results in increased light scatter that is converted to a peak rate signal as a function of the marker concentration, are suitable for use in the present invention. Nephelometry assays are commercially available from Beckman Coulter (Brea, Calif.; Kit #449430) and can be performed using a Behring Nephelometer Analyzer (Fink et al., *J. Clin. Chem. Clin. Biol. Chem.*, 27:261-276 (1989)).

Antigen capture ELISA can be useful for determining the presence or level of one or more markers in a sample. For example, in an antigen capture ELISA, an antibody directed to a marker of interest is bound to a solid phase and sample is added such that the marker is bound by the antibody. After unbound proteins are removed by washing, the amount of bound marker can be quantitated using, e.g., a radioimmunoassay (see, e.g., Harlow and Lane, Antibodies: A Laboratory Manual, Cold Spring Harbor Laboratory, New York, 1988)). Sandwich ELISA can also be suitable for use in the present invention. For example, in a two-antibody sandwich assay, a first antibody is bound to a solid support, and the marker of interest is allowed to bind to the first antibody. The amount of the marker is quantitated by measuring the amount of a second antibody that binds the marker. The antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), and the like. An assay strip can be prepared by coating the antibody or a plurality of antibodies in an array on a solid support. This strip can then be dipped into the test sample and processed quickly through washes and detection steps to generate a measurable signal, such as a colored spot.

A radioimmunoassay using, for example, an iodine-125 ($^{125}$I) labeled secondary antibody (Harlow and Lane, supra) is also suitable for determining the presence or level of one or more markers in a sample. A secondary antibody labeled with a chemiluminescent marker can also be suitable for use in the present invention. A chemiluminescence assay using a chemiluminescent secondary antibody is suitable for sensitive, non-radioactive detection of marker levels. Such secondary antibodies can be obtained commercially from various sources, e.g., Amersham Lifesciences, Inc. (Arlington Heights, Ill.).

The immunoassays described above are particularly useful for determining the presence or level of one or more markers in a sample. As a non-limiting example, a fixed neutrophil ELISA is useful for determining whether a sample is positive for ANCA or for determining ANCA levels in a sample. Similarly, an ELISA using yeast cell wall phosphopeptidomannan is useful for determining whether a sample is positive for ASCA-IgA and/or ASCA-IgG, or for determining ASCA-IgA and/or ASCA-IgG levels in a sample. An ELISA using OmpC protein or a fragment thereof is useful for determining whether a sample is positive for anti-OmpC antibodies, or for determining anti-OmpC antibody levels in a sample. An ELISA using I2 protein or a fragment thereof is useful for determining whether a sample is positive for anti-I2 antibodies, or for determining anti-I2 antibody levels in a sample. An ELISA using flagellin protein or a fragment thereof is useful for determining whether a sample is positive for anti-flagellin antibodies, or for determining anti-flagellin antibody levels in a sample. In addition, the immunoassays described above are particularly useful for determining the presence or level of other markers in a sample.

Specific immunological binding of the antibody to the marker of interest can be detected directly or indirectly. Direct labels include fluorescent or luminescent tags, metals, dyes, radionuclides, and the like, attached to the antibody. An antibody labeled with iodine-125 ($^{125}$I) can be used for determining the levels of one or more markers in a sample. A chemiluminescence assay using a chemiluminescent antibody specific for the marker is suitable for sensitive, non-radioactive detection of marker levels. An antibody labeled with fluorochrome is also suitable for determining the levels of one or more markers in a sample. Examples of fluorochromes include, without limitation, DAPI, fluorescein, Hoechst 33258, R-phycocyanin, B-phycoerythrin, R-phycoerythrin, rhodamine, Texas red, and lissamine. Secondary antibodies linked to fluorochromes can be obtained commercially, e.g., goat F(ab')$_2$ anti-human IgG-FITC is available from Tago Immunologicals (Burlingame, Calif.).

Indirect labels include various enzymes well-known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. An urease detection system can be used with a substrate such as urea-bromocresol purple (Sigma Immunochemicals; St. Louis, Mo.). A useful secondary antibody linked to an enzyme can be obtained from a number of commercial sources, e.g., goat F(ab')$_2$ anti-human IgG-alkaline phosphatase can be purchased from Jackson ImmunoResearch (West Grove, Pa.).

A signal from the direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis of the amount of marker levels can be made using a spectrophotometer such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously.

Quantitative western blotting can also be used to detect or determine the presence or level of one or more markers in a sample. Western blots can be quantitated by well-known methods such as scanning densitometry or phosphorimaging. As a non-limiting example, protein samples are electrophoresed on 10% SDS-PAGE Laemmli gels. Primary murine monoclonal antibodies are reacted with the blot, and antibody binding can be confirmed to be linear using a preliminary slot blot experiment. Goat anti-mouse horseradish peroxidase-coupled antibodies (BioRad) are used as the secondary antibody, and signal detection performed using chemiluminescence, for example, with the Renaissance chemiluminescence kit (New England Nuclear; Boston, Mass.) according to the manufacturer's instructions. Autoradiographs of the blots are analyzed using a scanning densitometer (Molecular Dynamics; Sunnyvale, Calif.) and normalized to a positive control. Values are reported, for example, as a ratio between the actual value to the positive control (densitometric index). Such methods are well known in the art as described, for example, in Parra et al, *J. Vasc. Surg.*, 28:669-675 (1998).

Alternatively, a variety of immunohistochemical assay techniques can be used to determine the presence or level of one or more markers in a sample. The term immunohistochemical assay encompasses techniques that utilize the visual detection of fluorescent dyes or enzymes coupled (i.e., conjugated) to antibodies that react with the marker of interest using fluorescent microscopy or light microscopy and includes, without limitation, direct fluorescent antibody assay, indirect fluorescent antibody (IFA) assay, anticomplement immunofluorescence, avidin-biotin immunofluorescence, and immunoperoxidase assays. An IFA assay, for example, is useful for determining whether a sample is positive for ANCA, the level of ANCA in a sample, whether a sample is positive for pANCA, the level of pANCA in a sample, and/or an ANCA staining pattern (e.g., cANCA, pANCA, NSNA, and/or SAPPA staining pattern). The concentration of ANCA in a sample can be quantitated, e.g., through endpoint titration or through measuring the visual intensity of fluorescence compared to a known reference standard.

Alternatively, the presence or level of a marker of interest can be determined by detecting or quantifying the amount of the purified marker. Purification of the marker can be achieved, for example, by high pressure liquid chromatography (HPLC), alone or in combination with mass spectrometry (e.g., MALDI/MS, MALDI-TOF/MS, tandem MS, etc.). Qualitative or quantitative detection of a marker of interest can also be determined by well-known methods including, without limitation, Bradford assays, Coomassie blue staining, silver staining, assays for radiolabeled protein, and mass spectrometry.

The analysis of a plurality of markers may be carried out separately or simultaneously with one test sample. For separate or sequential assay of markers, suitable apparatuses include clinical laboratory analyzers such as the ElecSys (Roche), the AxSym (Abbott), the Access (Beckman), the ADVIA®, the CENTAUR® (Bayer), and the NICHOLS ADVANTAGE® (Nichols Institute) immunoassay systems. Preferred apparatuses or protein chips perform simultaneous assays of a plurality of markers on a single surface. Particularly useful physical formats comprise surfaces having a plurality of discrete, addressable locations for the detection of a plurality of different markers. Such formats include protein microarrays, or "protein chips" (see, e.g., Ng et al., *J. Cell Mol. Med.*, 6:329-340 (2002)) and certain capillary devices (see, e.g., U.S. Pat. No. 6,019,944). In these embodiments, each discrete surface location may comprise antibodies to immobilize one or more markers for detection at each location. Surfaces may alternatively comprise one or more discrete particles (e.g., microparticles or nanoparticles) immobilized at discrete locations of a surface, where the microparticles comprise antibodies to immobilize one or more markers for detection.

In addition to the above-described assays for determining the presence or level of various markers of interest, analysis of marker mRNA levels using routine techniques such as Northern analysis, reverse-transcriptase polymerase chain reaction (RT-PCR), or any other methods based on hybridization to a nucleic acid sequence that is complementary to a portion of the marker coding sequence (e.g., slot blot hybridization) are also within the scope of the present invention. Applicable PCR amplification techniques are described in, e.g., Ausubel et al., *Current Protocols in Molecular Biology*, John Wiley & Sons, Inc. New York (1999), Chapter 7 and Supplement 47; Theophilus et al., "PCR Mutation Detection Protocols," Humana Press, (2002); and Innis et al., *PCR Protocols*, San Diego, Academic Press, Inc. (1990). General nucleic acid hybridization methods are described in Anderson, "Nucleic Acid Hybridization," BIOS Scientific Publishers, 1999. Amplification or hybridization of a plurality of transcribed nucleic acid sequences (e.g., mRNA or cDNA) can also be performed from mRNA or cDNA sequences arranged in a microarray. Microarray methods are generally described in Hardiman, "Microarrays Methods and Applications: Nuts & Bolts," DNA Press, 2003; and Baldi et al., "DNA Microarrays and Gene Expression: From Experiments to Data Analysis and Modeling," Cambridge University Press, 2002.

Analysis of the genotype of a marker such as a genetic marker can be performed using techniques known in the art including, without limitation, polymerase chain reaction (PCR)-based analysis, sequence analysis, and electrophoretic analysis. A non-limiting example of a PCR-based analysis includes a Taqman® allelic discrimination assay available from Applied Biosystems. Non-limiting examples of sequence analysis include Maxam-Gilbert sequencing, Sanger sequencing, capillary array DNA sequencing, thermal cycle sequencing (Sears et al., *Biotechniques*, 13:626-633 (1992)), solid-phase sequencing (Zimmerman et al., *Methods Mol. Cell. Biol.*, 3:39-42 (1992)), sequencing with mass spectrometry such as matrix-assisted laser desorption/ionization time-of-flight mass spectrometry (MALDI-TOF/MS; Fu et al., *Nature Biotech.*, 16:381-384 (1998)), and sequencing by hybridization (Chee et al., *Science*, 274:610-614 (1996); Drmanac et al., *Science*, 260:1649-1652 (1993); Drmanac et al., *Nature Biotech.*, 16:54-58 (1998)). Non-limiting examples of electrophoretic analysis include slab gel electrophoresis such as agarose or polyacrylamide gel electrophoresis, capillary electrophoresis, and denaturing gradient gel electrophoresis. Other methods for genotyping an individual at a polymorphic site in a marker include, e.g., the INVADER® assay from Third Wave Technologies, Inc., restriction fragment length polymorphism (RFLP) analysis, allele-specific oligonucleotide hybridization, a heteroduplex mobility assay, and single strand conformational polymorphism (SSCP) analysis.

Several markers of interest may be combined into one test for efficient processing of a multiple of samples. In addition, one skilled in the art would recognize the value of testing multiple samples (e.g., at successive time points, etc.) from the same subject. Such testing of serial samples can allow the identification of changes in marker levels over time. Increases or decreases in marker levels, as well as the absence of change in marker levels, can also provide useful information to classify IBD or to differentiate between clinical subtypes of IBD.

A panel consisting of one or more of the markers described above may be constructed to provide relevant information related to the approach of the present invention for classifying a sample as being associated with IBD or a clinical subtype thereof. Such a panel may be constructed using 1, 2, 3, 4, 5, 6, 7, 8, 9, 10, 11, 12, 13, 14, 15, 16, 17, 18, 19, 20, 25, 30, 35, 40, or more individual markers. The analysis of a single marker or subsets of markers can also be carried out by one skilled in the art in various clinical settings. These include, but are not limited to, ambulatory, urgent care, critical care, intensive care, monitoring unit, inpatient, outpatient, physician office, medical clinic, and health screening settings.

The analysis of markers could be carried out in a variety of physical formats as well. For example, the use of microtiter plates or automation could be used to facilitate the processing of large numbers of test samples. Alternatively, single sample formats could be developed to facilitate treatment and diagnosis in a timely fashion.

VII. Statistical Algorithms

In some aspects, the present invention provides methods, systems, and code for classifying whether a sample is associated with IBD using a statistical algorithm or process to classify the sample as an IBD sample or non-IBD sample. In other aspects, the present invention provides methods, systems, and code for classifying whether a sample is associated with a clinical subtype of IBD (i.e., differentiating between CD or UC) using a statistical algorithm or process to classify the sample as a CD sample, UC sample, or non-IBD sample. Preferably, the statistical algorithms or processes independently comprise one or more learning statistical classifier systems. As described herein, a combination of learning statistical classifier systems advantageously provides improved sensitivity, specificity, negative predictive value, positive predictive value, and/or overall accuracy for classifying whether a sample is associated with IBD or a clinical subtype thereof.

The term "statistical algorithm" or "statistical process" includes any of a variety of statistical analyses used to determine relationships between variables. In the present invention, the variables are the presence or level of at least one marker of interest. Any number of markers can be analyzed using a statistical algorithm described herein. For example, the presence or levels of 1, 2, 3, 4, 5, 6, 7, 8, 9, 10, 11, 12, 13, 14, 15, 16, 17, 18, 19, 20, 25, 30, 35, 40, 45, 50, or more markers can be included in a statistical algorithm. In one embodiment, logistic regression is used. In another embodiment, linear regression is used. In certain instances, the statistical algorithms of the present invention can use a quantile measurement of a particular marker within a given population as a variable. Quantiles are a set of "cut points" that divide a sample of data into groups containing (as far as possible) equal numbers of observations. For example, quartiles are values that divide a sample of data into four groups containing (as far as possible) equal numbers of observations. The lower quartile is the data value a quarter way up through the ordered data set; the upper quartile is the data value a quarter way down through the ordered data set. Quintiles are values that divide a sample of data into five groups containing (as far as possible) equal numbers of observations. The present invention can also include the use of percentile ranges of marker levels (e.g., tertiles, quartile, quintiles, etc.), or their cumulative indices (e.g., quartile sums of marker levels, etc.) as variables in the algorithms (just as with continuous variables).

Preferably, the statistical algorithms of the present invention comprise one or more learning statistical classifier systems. As used herein, the term "learning statistical classifier system" includes a machine learning algorithmic technique capable of adapting to complex data sets (e.g., panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naïve learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ).

Random forests are learning statistical classifier systems that are constructed using an algorithm developed by Leo Breiman and Adele Cutler. Random forests use a large number of individual decision trees and decide the class by choosing the mode (i.e., most frequently occurring) of the classes as determined by the individual trees. Random forest analysis can be performed, e.g., using the RandomForests software available from Salford Systems (San Diego, Calif.). See, e.g., Breiman, *Machine Learning*, 45:5-32 (2001); and http://stat-www.berkeley.edu/users/breiman/RandomForests/cc_home.htm, for a description of random forests.

Classification and regression trees represent a computer intensive alternative to fitting classical regression models and are typically used to determine the best possible model for a categorical or continuous response of interest based upon one or more predictors. Classification and regression tree analysis can be performed, e.g., using the C&RT software available from Salford Systems or the Statistica data analysis software available from StatSoft, Inc. (Tulsa, Okla.). A description of classification and regression trees is found, e.g., in Breiman et al. "Classification and Regression Trees," Chapman and Hall, New York (1984); and Steinberg et al., "CART: Tree-Structured Non-Parametric Data Analysis," Salford Systems, San Diego, (1995).

Neural networks are interconnected groups of artificial neurons that use a mathematical or computational model for information processing based on a connectionist approach to computation. Typically, neural networks are adaptive systems that change their structure based on external or internal information that flows through the network. Specific examples of neural networks include feed-forward neural networks such as perceptrons, single-layer perceptrons, multi-layer perceptrons, backpropagation networks, ADALINE networks, MADALINE networks, Learnmatrix networks, radial basis function (RBF) networks, and self-organizing maps or Kohonen self-organizing networks; recurrent neural networks such as simple recurrent networks and Hopfield networks; stochastic neural networks such as Boltzmann machines; modular neural networks such as committee of machines and associative neural networks; and other types of networks such as instantaneously trained neural networks, spiking neural networks, dynamic neural networks, and cascading neural networks. Neural network analysis can be performed, e.g., using the Statistica data analysis software available from StatSoft, Inc. See, e.g., Freeman et al., In "Neural Networks: Algorithms, Applications and Programming Techniques," Addison-Wesley Publishing Company (1991); Zadeh, Information and Control, 8:338-353 (1965); Zadeh, "IEEE Trans. on Systems, Man and Cybernetics," 3:28-44 (1973); Gersho et al., In "Vector Quantization and Signal Compression," Kluywer Academic Publishers, Boston, Dordrecht, London (1992); and Hassoun, "Fundamentals of Artificial Neural Networks," MIT Press, Cambridge, Mass., London (1995), for a description of neural networks.

Support vector machines are a set of related supervised learning techniques used for classification and regression and are described, e.g., in Cristianini et al., "An Introduction to Support Vector Machines and Other Kernel-Based Learning Methods," Cambridge University Press (2000). Support vector machine analysis can be performed, e.g., using the SVM$^{light}$ software developed by Thorsten Joachims (Cornell University) or using the LIBSVM software developed by Chih-Chung Chang and Chih-Jen Lin (National Taiwan University).

The learning statistical classifier systems described herein can be trained and tested using a cohort of samples (e.g., serological samples) from healthy individuals and IBD patients. For example, samples from patients diagnosed by a physician, and preferably by a gastroenterologist, as having IBD using a biopsy, colonoscopy, or an immunoassay as described in, e.g., U.S. Pat. No. 6,218,129, are suitable for use in training and testing the learning statistical classifier systems of the present invention. Samples from patients diagnosed with IBD can also be stratified into Crohn's disease or ulcerative colitis using an immunoassay as described in, e.g., U.S. Pat. Nos. 5,750,355 and 5,830,675. Samples from healthy individuals can include those that were not identified as IBD samples. One skilled in the art will know of additional techniques and diagnostic criteria for obtaining a cohort of patient samples that can be used in training and testing the learning statistical classifier systems of the present invention.

As used herein, the term "sensitivity" refers to the probability that a diagnostic method, system, or code of the present invention gives a positive result when the sample is positive, e.g., having IBD or a clinical subtype thereof. Sensitivity is calculated as the number of true positive results divided by the sum of the true positives and false negatives. Sensitivity essentially is a measure of how well a method, system, or code of the present invention correctly identifies those with IBD or a clinical subtype thereof from those without the disease. The statistical algorithms can be selected such that the sensitivity of classifying IBD or a clinical subtype thereof (e.g., CD or UC) is at least about 60%, and can be, for example, at least about 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. In preferred embodiments, the sensitivity of classifying IBD or a clinical subtype thereof is at least about 90% when a combination of learning statistical classifier systems is used (see, Example 6).

The term "specificity" refers to the probability that a diagnostic method, system, or code of the present invention gives a negative result when the sample is not positive, e.g., not having IBD or a clinical subtype thereof. Specificity is calculated as the number of true negative results divided by the sum of the true negatives and false positives. Specificity essentially is a measure of how well a method, system, or code of the present invention excludes those who do not have IBD or a clinical subtype thereof from those who have the disease. The statistical algorithms can be selected such that the specificity of classifying IBD or a clinical subtype thereof (e.g., CD or UC) is at least about 70%, for example, at least about 75%, 80%, 85%, 86%, 87%, 88%, 89%, 90%, 91%, 92%, 93%, 94%, 95%, 96%, 97%, 98%, or 99%. In preferred embodiments, the specificity of classifying IBD or a clinical subtype thereof is at least about 90% when a combination of learning statistical classifier systems is used (see, Example 6).

As used herein, the term "negative predictive value" or "NPV" refers to the probability that an individual identified as not having IBD or a clinical subtype thereof actually does not have the disease. Negative predictive value can be calculated as the number of true negatives divided by the sum of the true negatives and false negatives. Negative predictive value is determined by the characteristics of the diagnostic method, system, or code as well as the prevalence of the disease in the population analyzed. The statistical algorithms can be selected such that the negative predictive value in a population having a disease prevalence is in the range of about 70% to about 99% and can be, for example, at least about 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. In preferred embodiments, the negative predictive value of classifying IBD or a clinical subtype thereof is at least about 78% when a combination of learning statistical classifier systems is used (see, Example 6).

The term "positive predictive value" or "PPV" refers to the probability that an individual identified as having IBD or a clinical subtype thereof actually has the disease. Positive predictive value can be calculated as the number of true positives divided by the sum of the true positives and false positives. Positive predictive value is determined by the characteristics of the diagnostic method, system, or code as well as the prevalence of the disease in the population analyzed. The statistical algorithms can be selected such that the positive predictive value in a population having a disease prevalence is in the range of about 80% to about 99% and can be, for example, at least about 80%, 85%, 86%, 87%, 88%, 89%, 90%, 91%, 92%, 93%, 94%, 95%, 96%, 97%, 98%, or 99%. In preferred embodiments, the positive predictive value of classifying IBD or a clinical subtype thereof is at least about 86% when a combination of learning statistical classifier systems is used (see, Example 6).

Predictive values, including negative and positive predictive values, are influenced by the prevalence of the disease in the population analyzed. In the methods, systems, and code of the present invention, the statistical algorithms can be selected to produce a desired clinical parameter for a clinical population with a particular IBD prevalence. For example, learning statistical classifier systems can be selected for an IBD prevalence of up to about 1%, 2%, 3%, 4%, 5%, 6%, 7%, 8%, 9%, 10%, 15%, 20%, 25%, 30%, 35%, 40%, 45%, 50%, 55%, 60%, 65%, or 70%, which can be seen, e.g., in a clinician's office such as a gastroenterologist's office or a general practitioner's office.

As used herein, the term "overall agreement" or "overall accuracy" refers to the accuracy with which a method, system, or code of the present invention classifies a disease state. Overall accuracy is calculated as the sum of the true positives and true negatives divided by the total number of sample results and is affected by the prevalence of the disease in the population analyzed. For example, the statistical algorithms can be selected such that the overall accuracy in a patient population having a disease prevalence is at least about 60%, and can be, for example, at least about 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. In preferred embodiments, the overall accuracy of classifying IBD or a clinical subtype thereof is at least about 90% (e.g., 92%) when a combination of learning statistical classifier systems is used.

VIII. Disease Classification System

FIG. 1 illustrates a disease classification system (DCS) (100) according to one embodiment of the present invention. As shown therein, a DCS includes a DCS intelligence module (105), such as a computer, having a processor (115) and memory module (110). The intelligence module also includes communication modules (not shown) for transmitting and receiving information over one or more direct connections (e.g., USB, Firewire, or other interface) and one or more network connections (e.g., including a modem or other network interface device). The memory module may include internal memory devices and one or more external memory devices. The intelligence module also includes a display module (125), such as a monitor or printer. In one aspect, the intelligence module receives data such as patient test results from a data acquisition module such as a test system (150), either through a direct connection or over a network (140). For example, the test system may be configured to run multianalyte tests on one or more patient samples (155) and automatically provide the test results to the intelligence module. The data may also be provided to the intelligence module via direct input by a user or it may be downloaded from a portable medium such as a compact disk (CD) or a digital versatile disk (DVD). The test system may be integrated with the intelligence module, directly coupled to the intelligence module, or it may be remotely coupled with the intelligence module over the network. The intelligence module may also communicate data to and from one or more client systems (130) over the network as is well known. For example, a requesting physician or healthcare provider may obtain and view a report from the intelligence module, which may be resident in a laboratory or hospital, using a client system (130).

The network can be a LAN (local area network), WAN (wide area network), wireless network, point-to-point network, star network, token ring network, hub network, or other configuration. As the most common type of network in current use is a TCP/IP (Transfer Control Protocol and Internet Protocol) network such as the global internetwork of networks often referred to as the "Internet" with a capital "I," that will be used in many of the examples herein, but it should be understood that the networks that the present invention might use are not so limited, although TCP/IP is the currently preferred protocol.

Several elements in the system shown in FIG. 1 may include conventional, well-known elements that need not be explained in detail here. For example, the intelligence module could be implemented as a desktop personal computer, workstation, mainframe, laptop, etc. Each client system could include a desktop personal computer, workstation, laptop, PDA, cell phone, or any WAP-enabled device or any other computing device capable of interfacing directly or indirectly to the Internet or other network connection. A client system typically runs an HTTP client, e.g., a browsing program, such as Microsoft's Internet Explorer™ browser, Netscape's Navigator™ browser, Opera's browser, or a WAP-enabled browser in the case of a cell phone, PDA or other wireless device, or the like, allowing a user of the client system to access, process, and view information and pages available to it from the intelligence module over the network. Each client system also typically includes one or more user interface devices, such as a keyboard, a mouse, touch screen, pen or the like, for interacting with a graphical user interface (GUI) provided by the browser on a display (e.g., monitor screen, LCD display, etc.) (135) in conjunction with pages, forms, and other information provided by the intelligence module. As discussed above, the present invention is suitable for use with the Internet, which includes a specific global internetwork of networks. However, it should be understood that other networks can be used instead of the Internet, such as an intranet, an extranet, a virtual private network (VPN), a non-TCP/IP based network, any LAN or WAN, or the like.

According to one embodiment, each client system and all of its components are operator configurable using applications, such as a browser, including computer code run using a central processing unit such as an Intel Pentium processor or the like. Similarly, the intelligence module and all of its components might be operator configurable using application(s) including computer code run using a central processing unit (115) such as an Intel Pentium processor or the like, or multiple processor units. Computer code for operating and configuring the intelligence module to process data and test results as described herein is preferably downloaded and stored on a hard disk, but the entire program code, or portions thereof, may also be stored in any other volatile or non-volatile memory medium or device as is well known, such as a ROM or RAM, or provided on any other computer readable medium (160) capable of storing program code, such as a compact disk (CD) medium, digital versatile disk (DVD) medium, a floppy disk, ROM, RAM, and the like.

The computer code for implementing various aspects and embodiments of the present invention can be implemented in any programming language that can be executed on a computer system such as, for example, in C, C++, C#, HTML, Java, JavaScript, or any other scripting language, such as VBScript. Additionally, the entire program code, or portions thereof, may be embodied as a carrier signal, which may be transmitted and downloaded from a software source (e.g., server) over the Internet, or over any other conventional network connection as is well known (e.g., extranet, VPN, LAN, etc.) using any communication medium and protocols (e.g., TCP/IP, HTTP, HTTPS, Ethernet, etc.) as are well known.

According to one embodiment, the intelligence module implements a disease classification process for analyzing patient test results to determine whether a patient sample is associated with IBD or a clinical subtype thereof. The data may be stored in one or more data tables or other logical data structures in memory (110) or in a separate storage or database system coupled with the intelligence module. A statistical process is applied to a data set including test data for the patient sample. In one aspect, for example, the test data might include data indicating the presence or level of at least one marker in the patient sample. The statistical process produces a statistically derived decision classifying the patient sample as an IBD (e.g., CD or UC) sample or non-IBD sample based upon the presence or level of the at least one marker. The statistically derived decision may be displayed on a display device associated with or coupled to the intelligence module, or the decision may be provided to and displayed at a separate system, e.g., a client system (130). The displayed results allow a physician to make a reasoned diagnosis.

IX. Therapy and Therapeutic Monitoring

Once a sample from an individual has been classified as an IBD (e.g., CD or UC) sample, the methods, systems, and code of the present invention can further comprise administering to the individual a therapeutically effective amount of a drug useful for treating one or more symptoms associated with IBD or the IBD subtype. For therapeutic applications, the IBD drug can be administered alone or co-administered in combination with one or more additional IBD drugs and/or one or more drugs that reduce the side-effects associated with the IBD drug.

IBD drugs can be administered with a suitable pharmaceutical excipient as necessary and can be carried out via any of the accepted modes of administration. Thus, administration can be, for example, intravenous, topical, subcutaneous, transcutaneous, transdermal, intramuscular, oral, buccal, sublingual, gingival, palatal, intra-joint, parenteral, intra-arteriole, intradermal, intraventricular, intracranial, intraperitoneal, intralesional, intranasal, rectal, vaginal, or by inhalation. By "co-administer" it is meant that an IBD drug is administered at the same time, just prior to, or just after the administration of a second drug (e.g., another IBD drug, a drug useful for reducing the side-effects of the IBD drug, etc.).

A therapeutically effective amount of an IBD drug may be administered repeatedly, e.g., at least 2, 3, 4, 5, 6, 7, 8, or more times, or the dose may be administered by continuous infusion. The dose may take the form of solid, semi-solid, lyophilized powder, or liquid dosage forms, such as, for example, tablets, pills, pellets, capsules, powders, solutions, suspensions, emulsions, suppositories, retention enemas, creams, ointments, lotions, gels, aerosols, foams, or the like, preferably in unit dosage forms suitable for simple administration of precise dosages.

As used herein, the term "unit dosage form" includes physically discrete units suitable as unitary dosages for human subjects and other mammals, each unit containing a predetermined quantity of an IBD drug calculated to produce the desired onset, tolerability, and/or therapeutic effects, in association with a suitable pharmaceutical excipient (e.g., an ampoule). In addition, more concentrated dosage forms may be prepared, from which the more dilute unit dosage forms may then be produced. The more concentrated dosage forms thus will contain substantially more than, e.g., at least 1, 2, 3, 4, 5, 6, 7, 8, 9, 10, or more times the amount of the IBD drug.

Methods for preparing such dosage forms are known to those skilled in the art (see, e.g., REMINGTON'S PHARMACEUTICAL SCIENCES, 18TH ED., Mack Publishing Co., Easton, Pa. (1990)). The dosage forms typically include a conventional pharmaceutical carrier or excipient and may additionally include other medicinal agents, carriers, adjuvants, diluents, tissue permeation enhancers, solubilizers, and the like. Appropriate excipients can be tailored to the particular dosage form and route of administration by methods well known in the art (see, e.g., REMINGTON'S PHARMACEUTICAL SCIENCES, supra).

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols, e.g., Carbopol 941, Carbopol 980, Carbopol 981, etc. The dosage forms can additionally include lubricating agents such as talc, magnesium stearate, and mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; and flavoring agents. The dosage forms may also comprise biodegradable polymer beads, dextran, and cyclodextrin inclusion complexes.

For oral administration, the therapeutically effective dose can be in the form of tablets, capsules, emulsions, suspensions, solutions, syrups, sprays, lozenges, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

In some embodiments, the therapeutically effective dose takes the form of a pill, tablet, or capsule, and thus, the dosage form can contain, along with an IBD drug, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof. An IBD drug can also be formulated into a suppository disposed, for example, in a polyethylene glycol (PEG) carrier.

Liquid dosage forms can be prepared by dissolving or dispersing an IBD drug and optionally one or more pharmaceutically acceptable adjuvants in a carrier such as, for example, aqueous saline (e.g., 0.9% w/v sodium chloride), aqueous dextrose, glycerol, ethanol, and the like, to form a solution or suspension, e.g., for oral, topical, or intravenous administration. An IBD drug can also be formulated into a retention enema.

For topical administration, the therapeutically effective dose can be in the form of emulsions, lotions, gels, foams, creams, jellies, solutions, suspensions, ointments, and transdermal patches. For administration by inhalation, an IBD drug can be delivered as a dry powder or in liquid form via a nebulizer. For parenteral administration, the therapeutically effective dose can be in the form of sterile injectable solutions and sterile packaged powders. Preferably, injectable solutions are formulated at a pH of from about 4.5 to about 7.5.

The therapeutically effective dose can also be provided in a lyophilized form. Such dosage forms may include a buffer, e.g., bicarbonate, for reconstitution prior to administration, or the buffer may be included in the lyophilized dosage form for reconstitution with, e.g., water. The lyophilized dosage form may further comprise a suitable vasoconstrictor, e.g., epinephrine. The lyophilized dosage form can be provided in a syringe, optionally packaged in combination with the buffer for reconstitution, such that the reconstituted dosage form can be immediately administered to an individual.

In therapeutic use for the treatment of IBD or a clinical subtype thereof, an IBD drug can be administered at the initial dosage of from about 0.001 mg/kg to about 1000 mg/kg daily. A daily dose range of from about 0.01 mg/kg to about 500 mg/kg, from about 0.1 mg/kg to about 200 mg/kg, from about 1 mg/kg to about 100 mg/kg, or from about 10 mg/kg to about 50 mg/kg, can be used. The dosages, however, may be varied depending upon the requirements of the individual, the severity of IBD symptoms, and the IBD drug being employed. For example, dosages can be empirically determined considering the severity of IBD symptoms in an individual classified as having IBD according to the methods described herein. The dose administered to an individual, in the context of the present invention, should be sufficient to affect a beneficial therapeutic response in the individual over time. The size of the dose can also be determined by the existence, nature, and extent of any adverse side-effects that accompany the administration of a particular IBD drug in an individual. Determination of the proper dosage for a particular situation is within the skill of the practitioner. Generally, treatment is initiated with smaller dosages which are less than the optimum dose of the IBD drug. Thereafter, the dosage is increased by small increments until the optimum effect under circumstances is reached. For convenience, the total daily dosage may be divided and administered in portions during the day, if desired.

As used herein, the term "IBD drug" includes all pharmaceutically acceptable forms of a drug that is useful for treating one or more symptoms associated with IBD. For example, the IBD drug can be in a racemic or isomeric mixture, a solid complex bound to an ion exchange resin, or the like. In addition, the IBD drug can be in a solvated form. The term is also intended to include all pharmaceutically acceptable salts, derivatives, and analogs of the IBD drug being described, as well as combinations thereof. For example, the pharmaceutically acceptable salts of an IBD drug include, without limitation, the tartrate, succinate, tartarate, bitartarate, dihydrochloride, salicylate, hemisuccinate, citrate, maleate, hydrochloride, carbamate, sulfate, nitrate, and benzoate salt forms thereof, as well as combinations thereof and the like.

Any form of an IBD drug is suitable for use in the methods of the present invention, e.g., a pharmaceutically acceptable salt of an IBD drug, a free base of an IBD drug, or a mixture thereof.

Suitable drugs that are useful for treating one or more symptoms associated with IBD or a clinical subtype thereof include, but are not limited to, aminosalicylates (e.g., mesalazine, sulfasalazine, and the like), corticosteroids (e.g., prednisone), thiopurines (e.g., azathioprine, 6-mercaptopurine, and the like), methotrexate, monoclonal antibodies (e.g., infliximab), free bases thereof, pharmaceutically acceptable salts thereof, derivatives thereof, analogs thereof, and combinations thereof. One skilled in the art will know of additional IBD drugs suitable for use in the present invention (see, e.g., Sands, *Surg. Clin. North Am.*, 86:1045-1064 (2006); Danese et al., *Mini Rev. Med. Chem.*, 6:771-784 (2006); Domenech, *Digestion*, 73 (Suppl. 1):67-76 (2006); Nakamura et al., *World J. Gastroenterol.*, 12:4628-4635 (2006); and Gionchetti et al., *World J. Gastroenterol.*, 12:3306-3313 (2006)).

An individual can also be monitored at periodic time intervals to assess the efficacy of a certain therapeutic regimen once a sample from the individual has been classified as an IBD (e.g., CD or UC) sample. For example, the levels of certain markers change based on the therapeutic effect of a treatment such as a drug. The patient is monitored to assess response and understand the effects of certain drugs or treatments in an individualized approach. Additionally, patients may not respond to a drug, but the markers may change, suggesting that these patients belong to a special population (not responsive) that can be identified by their marker levels. These patients can be discontinued on their current therapy and alternative treatments prescribed.

X. EXAMPLES

The following examples are offered to illustrate, but not to limit, the claimed invention.

Example 1

Determination of ANCA Levels

This example illustrates an analysis of ANCA levels in a sample using an ELISA assay.

A fixed neutrophil enzyme-linked immunosorbent assay (ELISA) was used to detect ANCA as described in Saxon et al., *J. Allergy Clin. Immunol.*, 86:202-210 (1990). Briefly, microtiter plates were coated with $2.5 \times 10^5$ neutrophils per well from peripheral human blood purified by Ficoll-hypaque centrifugation and treated with 100% methanol for 10 minutes to fix the cells. Cells were incubated with 0.25% bovine serum albumin (BSA) in phosphate-buffered saline to block nonspecific antibody binding for 60 minutes at room temperature in a humidified chamber. Next, control and coded sera were added at a 1:100 dilution to the bovine serum/phosphate-buffered saline blocking buffer and incubated for 60 minutes at room temperature in a humidified chamber. Alkaline phosphatase-conjugated goat F(ab')$_2$ anti-human immunoglobulin G antibody (γ-chain specific; Jackson Immunoresearch Labs, Inc.; West Grove, Pa.) was added at a 1:1000 dilution to label neutrophil-bound antibody and incubated for 60 minutes at room temperature. A solution of p-nitrophenol phosphate substrate was added, and color development was allowed to proceed until absorbance at 405 nm in the positive control wells was 0.8-1.0 optical density units greater than the absorbance in blank wells.

A panel of twenty verified negative control samples was used with a calibrator with a defined ELISA Unit (EU) value. The base positive/negative cut-off for each ELISA run was defined as the optical density (OD) of the Calibrator minus the mean (OD) value for the panel of twenty negatives (plus 2 standard deviations) times the EU value of the Calibrator. The base cut-off value for ANCA reactivity was therefore about 10 to 20 EU, with any patient sample having an average EU value greater than the base cut-off marked as ELISA positive for ANCA reactivity. Similarly, a patient sample having an average EU value is less than or equal to the base cut-off is determined to be negative for ANCA reactivity.

Example 2

Determination of the Presence of pANCA

This example illustrates an analysis of the presence or absence of pANCA in a sample using an immunofluorescence assay as described, e.g., in U.S. Pat. Nos. 5,750,355 and 5,830,675. In particular, the presence of pANCA is detected by assaying for the loss of a positive value (e.g., loss of a detectable antibody marker and/or a specific cellular staining pattern as compared to a control) upon treatment of neutrophils with DNase.

Neutrophils isolated from a sample such as serum are immobilized on a glass side according to the following protocol:

1. Resuspend neutrophils in a sufficient volume of 1× Hanks' Balanced Salt Solution (HBSS) to achieve about $2.5 \times 10^6$ cells per ml.
2. Use a Cytospin3 centrifuge (Shandon, Inc.; Pittsburgh, Pa.) at 500 rpm for 5 minutes to apply 0.01 ml of the resuspended neutrophils to each slide.
3. Fix neutrophils to slide by incubating slides for 10 minutes in sufficient volume of 100% methanol to cover sample. Allow to air dry. The slides may be stored at −20° C.

The immobilized, fixed neutrophils are then treated with DNase as follows:

1. Prepare a DNase solution by combining 3 units of Promega RQ1™ DNase (Promega; Madison, Wis.) per ml buffer containing 40 mM of TRIS-HCl (pH 7.9), 10 mM of sodium chloride, 6 mM magnesium chloride, and 10 mM calcium chloride.
2. Rinse slides prepared using the above protocol with about 100 ml phosphate buffered saline (pH 7.0-7.4) for 5 minutes. Incubate immobilized neutrophils in 0.05 ml of DNase solution per slide for about 30 minutes at 37° C. Wash the slides three times with about 100-250 ml phosphate buffered saline at room temperature. The DNase reaction carried out as described herein causes substantially complete digestion of cellular DNA without significantly altering nuclear or cellular neutrophil morphology.

Next, an immunofluorescence assay is performed on the DNase-treated, fixed neutrophils according to the following protocol:

1. Add 0.05 ml of a 1:20 dilution of human sera in phosphate buffered saline to slides treated with DNase and to untreated slides. Add 0.05 ml phosphate buffered saline to clean slides as blanks. Incubate for about 0.5 to 1.0 hour at room temperature in sufficient humidity to minimize volume loss.
2. Rinse off sera by dipping into a container having 100-250 ml phosphate buffered saline.
3. Soak slide in phosphate buffered saline for 5 minutes. Blot lightly.

4. Add 0.05 ml goat F(ab')$_2$ anti-human IgG(μ)-FITC (Tago Immunologicals; Burlingame, Calif.), at a 1:1000 antibody:phosphate buffered saline dilution, to each slide. Incubate for 30 minutes at room temperature in sufficient humidity to minimize volume loss.
5. Rinse off antibody with 100-250 ml phosphate buffered saline. Soak slides for 5 minutes in 100-250 ml phosphate buffered saline, then allow to air dry.
6. Read fluorescence pattern on fluorescence microscope at 40×.
7. If desired, any DNA can be stained with propidium iodide stain by rinsing slides well with phosphate buffered saline at room temperature and stain for 10 seconds at room temperature. Wash slide three times with 100-250 ml phosphate buffered saline at room temperature and mount cover slip.

The immunofluorescence assay described above can be used to determine the presence of pANCA in DNase-treated, fixed neutrophils, e.g., by the presence of a pANCA reaction in control neutrophils (i.e., fixed neutrophils that have not been DNase-treated) that is abolished upon DNase treatment or by the presence of a pANCA reaction in control neutrophils that becomes cytoplasmic upon DNase treatment.

Example 3

Determination of ASCA Levels

This example illustrates the preparation of yeast cell well mannan and an analysis of ASCA levels in a sample using an ELISA assay.

Yeast cell wall mannan was prepared as described in Faille et al., *Eur. J. Clin. Microbiol. Infect. Dis.*, 11:438-446 (1992) and in Kocourek et al., *J. Bacteriol.*, 100:1175-1181 (1969). Briefly, a lyophilized pellet of yeast *Saccharomyces uvarum* was obtained from the American Type Culture Collection (#38926). Yeast were reconstituted in 10 ml 2×YT medium, prepared according to Sambrook et al., In "Molecular Cloning," Cold Spring Harbor Laboratory Press (1989). *S. uvarum* were grown for two to three days at 30° C. The terminal *S. uvarum* culture was inoculated on a 2×YT agar plate and subsequently grown for two to three days at 30° C. A single colony was used to inoculate 500 ml 2×YT media, and grown for two to three days at 30° C. Fermentation media (pH 4.5) was prepared by adding 20 g glucose, 2 g bacto-yeast extract, 0.25 g MgSO$_4$, and 2.0 ml 28% H$_3$PO$_4$ per liter of distilled water. The 500 ml culture was used to inoculate 50 liters of fermentation media, and the culture fermented for three to four days at 37° C.

*S. uvarum* mannan extract was prepared by adding 50 ml 0.02 M citrate buffer (5.88 g/l sodium citrate; pH 7.0±0.1) to each 100 g of cell paste. The cell/citrate mixture was autoclaved at 125° C. for ninety minutes and allowed to cool. After centrifuging at 5000 rpm for 10 minutes, the supernatant was removed and retained. The cells were then washed with 75 ml 0.02 M citrate buffer and the cell/citrate mixture again autoclaved at 125° C. for ninety minutes. The cell/citrate mixture was centrifuged at 5000 rpm for 10 minutes, and the supernatant was retained.

In order to precipitate copper/mannan complexes, an equal volume of Fehling's Solution was added to the combined supernatants while stirring. The complete Fehling's solution was prepared by mixing Fehling's Solution A with Fehling's Solution B in a 1:1 ratio just prior to use. The copper complexes were allowed to settle, and the liquid decanted gently from the precipitate. The copper/mannan precipitate complexes were then dissolved in 6-8 ml 3N HCl per 100 grams yeast paste.

The resulting solution was poured with vigorous stirring into 100 ml of 8:1 methanol:acetic acid, and the precipitate allowed to settle for several hours. The supernatant was decanted and discarded, then the wash procedure was repeated until the supernatant was colorless, approximately two to three times. The precipitate was collected on a scintered glass funnel, washed with methanol, and air dried overnight. On some occasions, the precipitate was collected by centrifugation at 5000 rpm for 10 minutes before washing with methanol and air drying overnight. The dried mannan powder was dissolved in distilled water to a concentration of approximately 2 g/ml.

A *S. uvarum* mannan ELISA was used to detect ASCA. *S. uvarum* mannan ELISA plates were saturated with antigen as follows. Purified *S. uvarum* mannan prepared as described above was diluted to a concentration of 100 μg/ml with phosphate buffered saline/0.2% sodium azide. Using a multichannel pipettor, 100 μl of 100 μg/ml *S. uvarum* mannan was added per well of a Costar 96-well hi-binding plate (catalog no. 3590; Costar Corp., Cambridge, Mass.). The antigen was allowed to coat the plate at 4° C. for a minimum of 12 hours. Each lot of plates was compared to a previous lot before use. Plates were stored at 2-8° C. for up to one month.

Patient sera were analyzed in duplicate for ASCA-IgA or ASCA-IgG reactivity. Microtiter plates saturated with antigen as described above were incubated with phosphate buffered saline/0.05% Tween-20 for 45 minutes at room temperature to inhibit nonspecific antibody binding. Patient sera were subsequently added at a dilution of 1:80 for analysis of ASCA-IgA and 1:800 for analysis of ASCA-IgG and incubated for 1 hour at room temperature. Wells were washed three times with PBS/0.05% Tween-20. Then, a 1:1000 dilution of alkaline phosphatase-conjugated goat anti-human IgA (Jackson Immunoresearch; West Grove, Pa.) or a 1:1000 dilution of alkaline phosphatase-conjugated goat anti-human IgG F(ab')$_2$ (Pierce; Rockford, Ill.) was added, and the microtiter plates were incubated for 1 hour at room temperature. A solution of p-nitrophenol phosphate in diethanolamine substrate buffer was added, and color development was allowed to proceed for 10 minutes. Absorbance at 405 nm was analyzed using an automated EMAX plate reader (Molecular Devices; Sunnyvale, Calif.).

To determine the base cut-off value for ASCA-IgA and ASCA-IgG, single point calibrators having fixed EU values were used. OD values for patient samples were compared to the OD value for the calibrators and multiplied by the calibrator assigned values. The base cut-off value for ASCA-IgA ELISA was 20 EU. The base cut-off value for ASCA-IgG was 40 EU.

Example 4

Determination of Anti-OmpC Antibody Levels

This example illustrates the preparation of OmpC protein and an analysis of anti-OmpC antibody levels in a sample using an ELISA assay.

The following protocol describes the purification of OmpC protein using spheroplast lysis. OmpF/OmpA-mutant *E. coli* were inoculated from a glycerol stock into 10-20 ml of Luria Bertani broth supplemented with 100 μg/ml streptomycin (LB-Strep; Teknova; Half Moon Bay, Calif.) and cultured vigorously at 37° C. for about 8 hours to log phase, followed by expansion to 1 liter in LB-Strep over 15 hours at 25° C. The cells were harvested by centrifugation. If necessary, cells are washed twice with 100 ml of ice cold 20 mM Tris-Cl, pH 7.5. The cells were subsequently resuspended in ice cold spheroplast forming buffer (20 mM Tris-Cl, pH 7.5; 20% sucrose; 0.1M EDTA, pH 8.0; 1 mg/ml lysozyme), after which the resuspended cells were incubated on ice for about 1 hour with occasional mixing by inversion. If required, the spheroplasts were centrifuged and resuspended in a smaller volume of spheroplast forming buffer (SFB). The spheroplast pellet was optionally frozen prior to resuspension in order to improve lysis efficiency. Hypotonic buffer was avoided in order to avoid bursting the spheroplasts and releasing chromosomal DNA, which significantly decreases the efficiency of lysis.

The spheroplast preparation was diluted 14-fold into ice cold 10 mM Tris-Cl, pH 7.5 containing 1 mg/ml DNaseI and was vortexed vigorously. The preparation was sonicated on ice 4×30 seconds at 50% power at setting 4, with a pulse "On time" of 1 second, without foaming or overheating the sample. Cell debris was pelleted by centrifugation and the supernatant was removed and clarified by centrifugation a second time. The supernatant was removed without collecting any part of the pellet and placed into ultracentrifuge tubes. The tubes were filled to 1.5 mm from the top with 20 mM Tris-Cl, pH 7.5. The membrane preparation was pelleted by ultracentrifugation at 100,000×g for 1 hr at 4° C. in a Beckman SW 60 swing bucket rotor. The pellet was resuspended by homogenizing into 20 mM Tris-Cl, pH 7.5 using a 1 ml pipette tip and squirting the pellet closely before pipetting up and down for approximately 10 minutes per tube. The material was extracted for 1 hr in 20 mM Tris-Cl, pH 7.5 containing 1% SDS, with rotation at 37° C. The preparation was transferred to ultracentrifugation tubes and the membrane was pelleted at 100,000×g. The pellet was resuspended by homogenizing into 20 mM Tris-Cl, pH 7.5 as before. The membrane preparation was optionally left at 4° C. overnight.

OmpC was extracted for 1 hr with rotation at 37° C. in 20 mM Tris-Cl, pH 7.5 containing 3% SDS and 0.5 M NaCl. The material was transferred to ultracentrifugation tubes and the membrane was pelleted by centrifugation at 100,000×g. The supernatant containing extracted OmpC was then dialyzed against more than 10,000 volumes to eliminate high salt content. SDS was removed by detergent exchange against 0.2% Triton. Triton was removed by further dialysis against 50 mM Tris-Cl. Purified OmpC, which functions as a porin in its trimeric form, was analyzed by SDS-PAGE. Electrophoresis at room temperature resulted in a ladder of bands of about 100 kDa, 70 kDa, and 30 kDa. Heating for 10-15 minutes at 65-70° C. partially dissociated the complex and resulted in only dimers and monomers (i.e., bands of about 70 kDa and 30 kDa). Boiling for 5 minutes resulted in monomers of 38 kDa.

The OmpC direct ELISA assays were performed essentially as follows. Plates (USA Scientific; Ocala, Fla.) were coated overnight at 4° C. with 100 µl/well OmpC at 0.25 µg/ml in borate buffered saline, pH 8.5. After three washes in 0.05% Tween 20 in phosphate buffered saline (PBS), the plates were blocked with 150 µl/well of 0.5% bovine serum albumin in PBS, pH 7.4 (BSA-PBS) for 30 minutes at room temperature. The blocking solution was then replaced with 100 µl/well of Crohn's disease or normal control serum, diluted 1:100. The plates were then incubated for 2 hours at room temperature and washed as before. Alkaline phosphatase-conjugated goat anti-human IgA (α-chain specific), or IgG (γ-chain specific) (Jackson ImmunoResearch; West Grove, Pa.) was added to the plates at a dilution of 1:1000 in BSA-PBS. The plates were incubated for 2 hours at room temperature before washing three times with 0.05% Tween 20/PBS followed by another three washes with Tris buffered normal saline, pH 7.5. Substrate solution (1.5 mg/ml disodium p-nitrophenol phosphate (Aresco; Solon, Ohio) in 2.5 mM $MgCl_2$, 0.01M Tris, pH 8.6) was added at 100 µl/well, and color was allowed to develop for one hour. The plates were then analyzed at 405 nm. IgA OmpC positive reactivity was defined as reactivity greater than two standard deviations above the mean reactivity obtained with control (normal) sera analyzed at the same time as the test samples.

Example 5

Determination of Anti-I2 Antibody Levels

This example illustrates the preparation of recombinant I2 protein and an analysis of anti-I2 antibody levels in a sample using an ELISA assay or a histological assay.

The full-length I2-encoding nucleic acid sequence was cloned into the GST expression vector pGEX. After expression in E. coli, the protein was purified on a GST column. The purified protein was shown to be of the expected molecular weight by silver staining, and had anti-GST reactivity upon Western blot analysis.

ELISA analysis was performed with the GST-I2 fusion polypeptide using diluted patient or normal sera. Reactivity was determined after subtracting reactivity to GST alone. Varying dilutions of Crohn's disease (CD) sera and sera from normal individuals were assayed for IgG reactivity to the GST-I2 fusion polypeptide. Dilutions of 1:100 to 1:1000 resulted in significantly higher anti-I2 polypeptide reactivity for the CD sera as compared to normal sera. These results indicate that the I2 protein is differentially reactive with CD sera as compared to normal sera.

Human IgA and IgG antibodies that bind the GST-I2 fusion polypeptide were detected by direct ELISA assays essentially as follows. Plates (Immulon 3; DYNEX Technologies; Chantilly, Va.) were coated overnight at 4° C. with 100 µl/well GST-I2 fusion polypeptide (5 µg/ml in borate buffered saline, pH 8.5). After three washes in 0.05% Tween 20 in phosphate buffered saline (PBS), the plates were blocked with 150 µl/well of 0.5% bovine serum albumin in PBS, pH 7.4 (BSA-PBS) for 30 minutes at room temperature. The blocking solution was then replaced with 100 µl/well of CD serum, ulcerative colitis (UC) serum, or normal control serum, diluted 1:100. The plates were then incubated for 2 hours at room temperature and washed as before. Alkaline phosphatase-conjugated secondary antibody (goat anti-human IgA (α-chain specific); Jackson ImmunoResearch; West Grove, Pa.) was added to the IgA plates at a dilution of 1:1000 in BSA-PBS. For IgG reactivity, alkaline phosphatase conjugated secondary antibody (goat anti-human IgG (γ-chain specific); Jackson ImmunoResearch) was added. The plates were incubated for 2 hours at room temperature before washing three times with 0.05% Tween 20/PBS followed by another three washes with Tris buffered normal saline, pH 7.5. Substrate solution (1.5 mg/ml disodium p-nitrophenol phosphate (Aresco; Solon, Ohio) in 2.5 mM $MgCl_2$, 0.01 M Tris, pH 8.6, was added at 100 µl/well, and color allowed to develop for one hour. The plates were then analyzed at 405 nm. Using a cutoff that is two standard deviations above the mean value for the normal population, nine of ten CD values were positive, while none of the normal serum samples were positive. Furthermore, seven of ten CD patients showed an $OD_{405}$ greater than 0.3, while none of the UC or normal samples were positive by this measure. These results indicate that immunoreactivity to the I2 polypeptide, in particular, IgA immunoreactivity, can be used to diagnose CD.

For histological analysis, rabbit anti-I2 antibodies were prepared using purified GST-I2 fusion protein as the immunogen. GST-binding antibodies were removed by adherence to GST bound to an agarose support (Pierce; Rockford, Ill.), and the rabbit sera validated for anti-I2 immunoreactivity by ELISA analysis. Slides were prepared from paraffin-embedded biopsy specimens from CD, UC, and normal controls. Hematoxylin and eosin staining were performed, followed by incubation with I2-specific antiserum. Binding of antibodies was detected with peroxidase-labeled anti-rabbit secondary antibodies (Pierce; Rockford, Ill.). The assay was optimized to maximize the signal to background and the distinction between CD and control populations.

Example 6

Combinatorial Statistical Algorithm for Predicting IBD

This example illustrates diagnostic algorithms derived from combining learning statistical classifier systems to classify whether a sample is associated with IBD or a clinical subtype thereof using a panel of serological markers.

A large cohort of serological samples from normal and diseased patients were used in this study and the levels and/or presence of a panel of various anti-bacterial antibody markers were measured to assess the diagnostic capability of the panel to identify patients with IBD and to selectively differentiate between UC and CD. Approximately 2,000 samples with an IBD prevalence between 60% to 64% were tested. The panel of serological markers included ANCA, ASCA-IgA, ASCA-IgG, anti-OmpC antibodies, anti-flagellin antibodies (e.g., anti-Cbir-1 antibodies), and pANCA. The levels of ANCA, ASCA-IGA, ASCA-IgG, anti-OmpC antibodies, and anti-flagellin antibodies were determined by ELISA. Indirect immunofluorescense microscopy was used to determine whether a sample was positive or negative for pANCA.

In this study, a novel approach was developed that uses a hybrid of different learning statistical classifier systems to predict IBD, CD, or UC based upon the levels and/or presence of a panel of serological markers. These learning statistical classifier systems use multivariate statistical methods like, for example, multilayer perceptrons with feed forward Back Propagation, that can adapt to complex data and make decisions based strictly on the data presented, without the constraints of regular statistical classifiers. In particular, a combinatorial approach that makes use of multiple discriminant functions by analyzing markers with more than one learning statistical classifier system was created to further improve the sensitivity and specificity of diagnosing IBD and differentiating between UC and CD. The model that performed with the greatest accuracy used an algorithm that was derived from a combination of decision/classification trees and neural networks.

The results from each of the six markers (i.e., ANCA levels, ASCA-IgA levels, ASCA-IgG levels, anti-OmpC antibody levels, anti-flagellin antibody levels, and pANCA-positivity or pANCA-negativity; "Predictors") and the diagnosis (0=Normal, 1=CD, 2=UC; "Dependent Variable 1") from a cohort of 587 patient samples were input into the classification and regression tree (C&RT) software module of Statistica Data Miner Version 7.1 (StatSoft, Inc.; Tulsa, Okla.). The data was split into training and testing, with 71% training samples and 29% testing samples. Different samples were used for training and testing.

Figure 2:
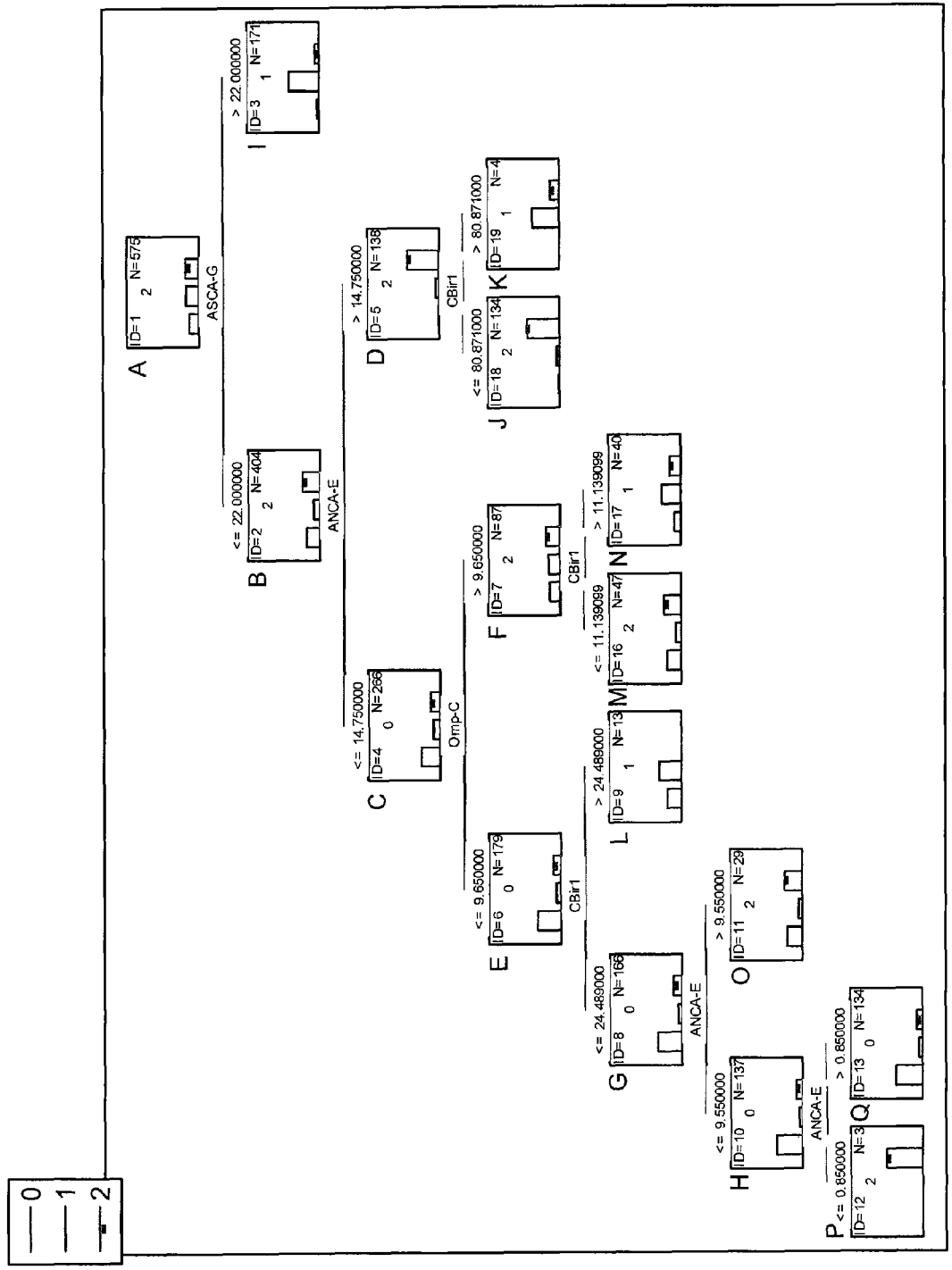
FIG. 2 shows the decision tree structure of a classification and regression tree (C&RT) for classifying IBD or a clinical subtype thereof (e.g., CD or UC) having 8 non-terminal nodes (A-H) and 9 terminal nodes (1-Q).

The data from the training dataset was used to produce RT-derived models using the default settings (i.e., standard C&RT) with all six markers. The C&RT method builds optimal decision tree structures consisting of nodes and likes that connect the nodes. As used herein, the terms "node" or "non-terminal node" or "non-terminal node value" refers to a decision point in the tree. The terms "terminal node" or "terminal node value" refers to non-leaf nodes without branches or final decisions. FIG. 2 provides an example of a C&RT structure for diagnosing IBD or a clinical subtype thereof (e.g., CD or UC) having 8 non-terminal nodes (A-H) and 9 terminal nodes (1-Q). The C&RT analysis also derives probability values for each prediction. These probability values are directly related to the node values. Node values are derived from the probability values for each sample.

The C&RT analysis was then validated using the testing sample set. Table 1 shows the results of the C&RT analysis on the testing samples.

TABLE 1

Classification matrix of the C&RT analysis on the testing sample set.

Classification matrix 1 (Learn_test_Dataset_Statsoft110205 in Workbook1)
Dependent variable: Diagnosis
Options: Categorical response, Test sample

|  | Observed | Predicted 0 | Predicted 1 | Predicted 2 | Row Total |
|---|---|---|---|---|---|
| Number | 0 | 30 | 11 | 19 | 60 |
| Column Percentage |  | 60.00% | 12.36% | 19.79% |  |
| Row Percentage |  | 50.00% | 18.33% | 31.67% |  |
| Total Percentage |  | 12.77% | 4.68% | 8.09% | 25.53% |
| Number | 1 | 11 | 67 | 11 | 89 |
| Column Percentage |  | 22.00% | 75.28% | 11.46% |  |
| Row Percentage |  | 12.36% | 75.28% | 12.36% |  |
| Total Percentage |  | 4.68% | 28.51% | 4.68% | 37.87% |
| Number | 2 | 9 | 11 | 66 | 86 |
| Column Percentage |  | 18.00% | 12.36% | 68.75% |  |
| Row Percentage |  | 10.47% | 12.79% | 76.74% |  |
| Total Percentage |  | 3.83% | 4.68% | 28.09% | 36.60% |
| Count | All Groups | 50 | 89 | 96 | 235 |
| Total Percent |  | 21.28% | 37.87% | 40.85% |  |

Normal samples = 0. Samples identified as CD = 1. Samples identified as UC = 2.

The data from the C&RT provided terminal nodes and probabilities associated with each sample that facilitated further prediction analysis (Table 2).

The Intelligent Problem Solver (IPS) was then selected from the NN software. The input variables from the training sample set were selected, including either the terminal nodes

TABLE 2

Predicted values, probabilities, and terminal nodes of the training sample set.

Predicted values 1 (Learn_test_Dataset_Statsoft110205 in Workbook1)
Dependent variable: Diagnosis
Options: Categorical response, Tree number 1, Analysis sample

|  | Observed value | Predicted value | Probability for 0 | Probability for 1 | Probability for 2 | Terminal node |
|---|---|---|---|---|---|---|
| SG07222043 | 0 | 0 | 0.738806 | 0.097015 | 0.164179 | 13 |
| SG07222005 | 0 | 0 | 0.738806 | 0.097015 | 0.164179 | 13 |
| SE11061100 | 0 | 0 | 0.738806 | 0.097015 | 0.164179 | 13 |
| SG07222028 | 0 | 2 | 0.413793 | 0.103448 | 0.482759 | 11 |
| SG07222010 | 0 | 0 | 0.738806 | 0.097015 | 0.164179 | 13 |
| SE11061064 | 0 | 1 | 0.384615 | 0.615385 | 0.000000 | 9 |
| SE11061062 | 0 | 0 | 0.738806 | 0.097015 | 0.164179 | 13 |
| SG07222118 | 0 | 0 | 0.738806 | 0.097015 | 0.164179 | 13 |
| SE11061094 | 0 | 1 | 0.175000 | 0.525000 | 0.300000 | 17 |
| SE11061084 | 0 | 0 | 0.738806 | 0.097015 | 0.164179 | 13 |
| SE11061045 | 0 | 2 | 0.413793 | 0.103448 | 0.482759 | 11 |
| SE11061089 | 0 | 0 | 0.738806 | 0.097015 | 0.164179 | 13 |
| SE11061121 | 0 | 0 | 0.738806 | 0.097015 | 0.164179 | 13 |
| SE11061054 | 0 | 0 | 0.738806 | 0.097015 | 0.164179 | 13 |
| SE11061120 | 0 | 2 | 0.382979 | 0.148936 | 0.468085 | 16 |
| SE11061071 | 0 | 1 | 0.384615 | 0.615385 | 0.000000 | 9 |
| SE11061109 | 0 | 0 | 0.738806 | 0.097015 | 0.164179 | 13 |
| SE11061068 | 0 | 0 | 0.738806 | 0.097015 | 0.164179 | 13 |
| SE11061046 | 0 | 2 | 0.382979 | 0.148936 | 0.468085 | 16 |
| SE11061081 | 0 | 0 | 0.738806 | 0.097015 | 0.164179 | 13 |

The terminal nodes and probability values for 0 (normal), 1 (CD), and 2 (UC) were saved along with the variables for use as input in the neural network (NN) analysis. Table 3 shows the marker variables and terminal nodes being used to predict diagnosis in the NN.

or the probability values. A column was added to the data to produce another dependent variable that identifies non-IBD (O) or IBD (1) and can be used to train the NN independently of the "Diagnosis Variable" (0=normal, 1=CD, and 2=UC). Diagnosis and IBD/non-IBD were used as the output depen-

TABLE 3

Marker variables and terminal node values used to predict diagnosis in the NN.

Predicted values 1
Dependent variable: Diagnosis
Options: Categorical response

|  | 1 ANCA ELISA | 2 Omp-C | 3 ASCA-IgA | 4 ASCA-IgG | 5 Cbir1 | 6 pANCA | 7 Diagnosis | 8 Terminal node |
|---|---|---|---|---|---|---|---|---|
| SG07222043 | 0.9 | 2.9 | 1.4 | 3.5 | 8.669 | 0 | 0 | 13.00000 |
| SG07222005 | 5.6 | 0.9 | 2.2 | 2.3 | 5.92 | 0 | 0 | 13.00000 |
| SE11061100 | 8.7 | 7.5 | 1.4 | 3.5 | 9.60099437 | 0 | 0 | 13.00000 |
| SG07222028 | 12.5 | 5.2 | 2.6 | 2.9 | 3.939 | 1 | 0 | 11.00000 |
| SG07222010 | 7.1 | 1.8 | 2.6 | 10 | 3.97 | 0 | 0 | 13.00000 |
| SE11061064 | 6.8 | 8.7 | 24 | 12.7 | 56.3576681 | 0 | 0 | 9.00000 |
| SE11061062 | 6.3 | 3.4 | 3.7 | 3.4 | 4.56971632 | 0 | 0 | 13.00000 |
| SG07222118 | 6.1 | 7.7 | 13.8 | 4.1 | 3.18 | 0 | 0 | 13.00000 |
| SE11061094 | 8.9 | 16.6 | 2.3 | 4.7 | 15.1623933 | 0 | 0 | 17.00000 |
| SE11061084 | 4.8 | 2.8 | 0.4 | 0.9 | 4.38862403 | 1 | 0 | 13.00000 |
| SE11061045 | 9.7 | 8.9 | 2.3 | 4.8 | 8.498928 | 0 | 0 | 11.00000 |
| SE11061089 | 5.9 | 8 | 5.6 | 4 | 5.62521943 | 0 | 0 | 13.00000 |
| SE11061121 | 7 | 5.3 | 2 | 6.3 | 4.24191095 | 0 | 0 | 13.00000 |
| SE11061054 | 5.7 | 7.2 | 5 | 2 | 8.53797967 | 0 | 0 | 13.00000 |
| SE11061120 | 8.7 | 19.1 | 7.8 | 2.5 | 6.93804629 | 0 | 0 | 16.00000 |
| SE11061071 | 6 | 6.8 | 4.1 | 3.1 | 25.8155087 | 0 | 0 | 9.00000 |
| SE11061109 | 5.9 | 6 | 4.1 | 10 | 5.90331709 | 0 | 0 | 13.00000 |
| SE11061068 | 6.3 | 8.5 | 4.5 | 1.9 | 8.90373603 | 0 | 0 | 13.00000 |
| SE11061046 | 8.5 | 17 | 5.2 | 3.6 | 10.215401 | 0 | 0 | 16.00000 |
| SE11061081 | 5.4 | 7.6 | 12.2 | 4.3 | 20.3574337 | 0 | 0 | 13.00000 | dent variables. Next, 1,000 Multilevel Perceptron NN models were created using the training sample set and terminal node or probability inputs. The best 100 models were selected and validated with the testing sample set. Assay precision was then calculated from the confusion matrix produced by the NN program using Microsoft Excel.

A comparison of the accuracy of IBD prediction by different statistical analyses and cut-off analysis is presented in Table 4. The best overall prediction of IBD is observed with the C&RT/NN hybrid algorithmic analysis.

TABLE 4

Comparison of IBD prediction accuracy by various methods.

| Type | Prediction | Sens.. | Spec. | PPV | NPV |
|---|---|---|---|---|---|
| Hybrid NN and C&RT | IBD | 90% | 90% | 86% | 78% |
| C&RT Alone | IBD | 88% | 81% | 89% | 79% |
| NN Alone | IBD | 83% | 83% | 88% | 76% |
| Logit Regression | IBD | 73% | 92% | 94% | 67% |
| Cutoff Analysis | IBD | 70% | 90% | 95% | 52% |

Figure 3:
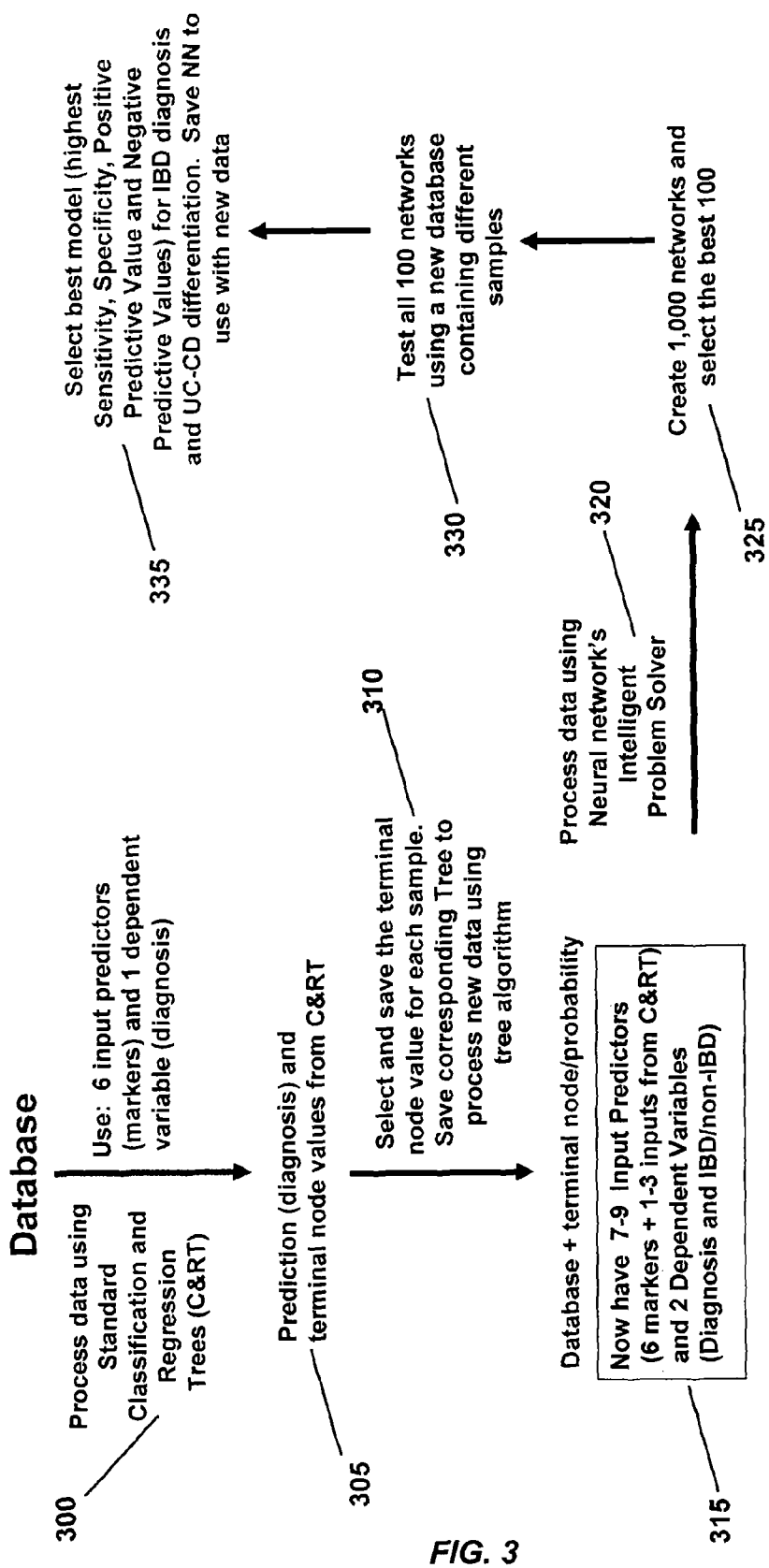
FIG. 3 shows a flowchart describing the algorithms derived from combining learning statistical classifiers for IBD diagnosis and CD/UC differentiation using a panel of serological markers.

FIG. 3 provides a summary of the above-described algorithmic models that were generated using the cohort of serological samples from normal and diseased patients. These models can then be used for analyzing samples from new patients to diagnose IBD or differentiate between CD and UC based upon the presence or level of one or more markers.

With reference to FIG. 3, a database (300) from a large cohort of serological samples derived from normal and diseased patients was used to measure the levels and/or presence of a panel of anti-bacterial antibody markers to create models that can be used to identify patients with IBD and to selectively distinguish between UC and CD. Specifically, for each sample, six input predictors (i.e., the six IBD markers described above) and 1 dependent variable (i.e., diagnosis) from the cohort of patient samples were processed using the C&RT software module of Statistica Data Miner Version 7.1. Diagnostic predictions, terminal node values (305), and probability values were obtained from the C&RT method. The terminal node and probability values for each sample were selected and saved and the corresponding tree (310) was saved for use as a C&RT model to process data from new patients using this algorithm. Next, the seven or 9 input predictors (i.e., the six IBD markers described above plus the terminal node, or plus the three probability values) and the dependent variable (315) were processed using the Intelligent Problem Solver program (320) from the NN software. 1,000 networks were created and the best 100 networks (325) were selected and validated. These 100 networks were validated with the test (330) database containing different samples. Finally, the best NN model (335) was selected as the one having the highest sensitivity, specificity, positive predictive value, and/or negative predictive value for diagnosing IBD and/or differentiating between CD and UC.

This NN model was saved for use in processing data from new patients using this algorithm to predict IBD, CD, or UC and/or to provide a probability that the patient has IBD, CD, or UC (e.g., about a 0%, 10%, 20%, 30%, 40%, 50%, 60%, 70%, 75%, 80%, 85%, 90%, 95%, or greater probability of having IBD). In essence, the C&RT and NN models generated from the cohort of patient samples are used in tandem to diagnose IBD or differentiate between CD and UC in a new patient based upon the presence or level of one or more markers in a sample from that patient.

FIG. 4 shows marker input variables, output dependent variables (Diagnosis and Non-IBD/IBD), and probabilities from a C&RT model used as input variables for the NN model. Row 7 (Non-IBD/IBD) was created from the diagnosis data to produce a second output that is predicted independently of the diagnosis.

Example 7

Analysis of IBD Serological Markers by an Algorithmic Approach Improves the Accuracy of Detecting Inflammatory Bowel Disease, Crohn's Disease and Ulcerative Colitis Serological testing can assist physicians in making a diagnosis of inflammatory bowel disease (IBD) and classifying the disease as Crohn's disease (CD) or ulcerative colitis (UC). Serological tests for IBD include for example, assays for ASCA (IgA and IgG), anti-Omp C, anti-CBir1 and pANCA. One algorithmic approach to IBD serological marker analysis described in this example is a sophisticated computer-aided analyses consisting of a statistical classifier followed by a neural network. In this example, assay results are not compared to cut off values, but rather disease and non disease patterns are detected by the algorithm. This example uses a cohort of 1813 serum samples with known diagnoses which was composed of 370 normals, 366 inflammatory bowel syndrome, 646 CD and 431 UC. The overall prevalence of IBD in this cohort was 59%. This cohort of samples was used to train the algorithm in pattern recognition. The resultant algorithm was then validated on a different sample population; none of the samples used in the development of the algorithm were used in the validation. The validation cohort had a 59% prevalence of IBD and consisted of 207 normals, 188 CD and 105 UC samples (total=500 samples). All of the CD and UC samples used in validation were from subjects who had confirmed disease. Overall the accuracy of the algorithm was 92%. Additional performance characteristics of the algorithm are shown below:

| Validation cohort (59%) | IBD | UC | CD |
|---|---|---|---|
| Sensitivity | 93% | 93% | 88% |
| Specificity | 95% | 97% | 98% |
| Positive Predictive Value | 96% | 89% | 96% |
| Negative Predictive Value | 90% | 98% | 93% |

Since positive and negative predictive values (PPV, NPV) vary with prevalence, these values were determined for a second validation cohort with a 15% prevalence of IBD consisting of 207 normals, 18 CD and 18 UC samples (total=243 samples). PPVs for IBD, UC and CD were 75%, 73% and 74% respectively; NPVs for IBD, UC and CD were 99%, 99% and 100% respectively. As shown herein, algorithmic analysis of serological data results in accurate detection of IBD and classification of IBD into CD and UC.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for classifying whether a sample from an individual is associated with inflammatory bowel disease (IBD), said method comprising:
   (a) analyzing a sample obtained from said individual to determine the presence or level of an anti-neutrophil cytoplasmic antibody (ANCA), anti-*Saccharomyces cerevisiae* immunoglobulin A (ASCA-IgA), anti-*Saccharomyces cerevisiae* immunoglobulin G (ASCA-IgG), an anti-outer membrane protein C (anti-OmpC) antibody, an anti-flagellin antibody, and a perinuclear anti-neutrophil cytoplasmic antibody (pANCA) in said sample; and
   (b) applying a combination of at least two learning statistical classifier systems in tandem to the presence or level of said ANCA, ASCA-IgA, ASCA-IgG, anti-OmpC antibody, anti-flagellin antibody, and pANCA determined in step (a) to classify said sample as an IBD sample or non-IBD sample with an overall accuracy of at least 70%, wherein said combination of at least two learning statistical classifier systems comprises a classification and regression tree (C&RT) or random forest and a neural network, and wherein said C&RT or random forest is first applied to the presence or level of said ANCA, ASCA-IgA, RSCA-IgG, anti-OmpC antibody, anti-flagellin antibody, and pANCA determined in step (a) to generate a prediction or probability value.

2. The method of claim 1, wherein the presence or level of said ANCA, ASCA-IgA, ASCA-IgG, anti-OmpC antibody, or anti-flagellin antibody is determined by assaying said sample with an immunoassay.

3. The method of claim 2, wherein said immunoassay is an enzyme-linked immunosorbent assay (ELISA).

4. The method of claim 1, wherein the presence or level of said pANCA is determined by assaying said sample with an immunohistochemical assay.

5. The method of claim 4, wherein said immunohistochemical assay is an immunoflourescence assay.

6. The method of claim 1, wherein said sample is selected from the group consisting of serum, plasma, whole blood, and stool.

7. The method of claim 1, wherein step (b) further comprises applying said neural network to said prediction or probability value and the presence or level of said ANCA, ASCA-IgA, ASCA-IgG, anti-OmpC antibody, anti-flagellin antibody, and pANCA determined in step (a) to classify said sample as an IBD sample or non-IBD sample.

8. The method of claim 1, wherein said method further comprises sending the results from said classification to a clinician.

9. The method of claim 1, wherein said method further provides a diagnosis in the form of a probability that said individual has IBD.

10. The method of claim 1, wherein said method further comprises administering to said individual a therapeutically effective amount of a drug useful for treating one or more symptoms associated with IBD.

11. The method of claim 10, wherein said drug is selected from the group consisting of aminosalicylates, corticosteroids, thiopurines, methotrexate, monoclonal antibodies, free bases thereof, pharmaceutically acceptable salts thereof, derivatives thereof, analogs thereof, and combinations thereof 12. A tangible computer-readable medium that stores code for controlling one or more processors to classify whether a sample from an individual is associated with IBD, said code including instructions to apply a statistical process comprising a combination of at least two learning statistical classifier systems in tandem to a data set indicating the presence or level of an anti-neutrophil cytoplasmic antibody (ANCA), anti-*Saccharomyces cerevisiae* immunoglobulin A (ASCA-IgA), anti-*Saccharomyces cerevisiae* immunoglobulin G (ASCA-IgG), an anti-outer membrane protein C (anti-OmpC) antibody, an anti-flagellin antibody, and a perinuclear anti-neutrophil cytoplasmic antibody (pANCA) in said sample to produce a statistically derived decision classifying said sample as an IBD sample or non-IBD sample based upon the presence or level of said ANCA, ASCA-IgA, ASCA-IgG, anti-OmpC antibody, anti-flagellin antibody, and pANCA to classify said sample as an IBD sample or non-IBD sample with an overall accuracy of at least 70%,
   wherein said combination of at least two learning statistical classifier systems comprises a classification and regression tree (C&RT) or random forest and a neural network, and
   wherein said C&RT or random forest is first applied to the presence or level of said ANCA, ASCA-IgA, ASCA-IgG, anti-OmpC antibody, anti-flagellin antibody, and pANCA to generate a prediction or probability value.

13. A system for classifying whether a sample from an individual is associated with IBD, said system comprising:
   (a) a data acquisition device configured to produce a data set indicating the presence or level of an anti-neutrophil cytoplasmic antibody (ANCA), anti-*Saccharomyces cerevisiae* immunoglobulin A (ASCA-IgA), anti-*Saccharomyces cerevisiae* immunoglobulin G (ASCA-IgG), an anti-outer membrane protein C (anti-OmpC) antibody, an anti-flagellin antibody, and a perinuclear anti-neutrophil cytoplasmic antibody (pANCA) in said sample;
   (b) a data processing device configured to process the data set by applying a statistical process comprising a combination of at least two learning statistical classifier systems in tandem to the data set to produce a statistically derived decision classifying said sample as an IBD sample or non-IBD sample based upon the presence or level of said ANCA, ASCA-IgA, ASCA-IgG, anti-OmpC antibody, anti-flagellin antibody, and pANCA to classify said sample as an IBD sample or non-IBD sample with an overall accuracy of at least 70%, wherein said combination of at least two learning statistical classifier systems comprises a classification and regression tree (C&RT) or random forest and a neural network, and wherein said C&RT or random forest is first applied to the data set to generate a prediction or probability value; and
   (c) a display device configured to display the statistically derived decision.

14. The method of claim 1, wherein step (a) further comprises analyzing said sample to determine the presence or level of an anti-I2 antibody.

15. The method of claim 1, wherein said anti-flagellin antibody is an anti-Cbir-1 antibody.

16. The method of claim 1, wherein said IBD sample is classified as a Crohn's disease (CD) sample or ulcerative colitis (UC) sample.

17. The method of claim 1, wherein said combination of at least two learning statistical classifier systems classifies said sample as an IBD sample or non-IBD sample with a sensitivity of at least 70%.

18. The method of claim 1, wherein said combination of at least two learning statistical classifier systems classifies said sample as an IBD sample or non-IBD sample with a specificity of at least 80%.

19. The method of claim 1, wherein said combination of at least two learning statistical classifier systems classifies said sample as an IBD sample or non-IBD sample with a positive predictive value (PPV) of at least 80%.

20. The method of claim 1, wherein said combination of at least two learning statistical classifier systems classifies said sample as an IBD sample or non-IBD sample with a negative predictive value (NPV) of at least 70%.

21. The method of claim 1, wherein the presence or level of said ANCA is determined by assaying the binding between said ANCA and fixed neutrophils.

22. The method of claim 1, wherein the presence or level of said ASCA-IgA or ASCA-IgG is determined by assaying the binding between said ASCA-IgA or ASCA-IgG and an antigen selected from the group consisting of yeast cell wall mannan, a purified oligomannoside antigen, a synthetic oligomannoside antigen, and combinations thereof 23. The method of claim 22 wherein said antigen is yeast cell wall phosphopeptidomannan (PPM).

24. The method of claim 23, wherein said yeast cell wall PPM is *S. uvarum* PPM.

25. The method of claim 1, wherein the presence or level of said anti-OmpC antibody is determined by assaying the binding between said anti-OmpC antibody and an OmpC protein or an immunoreactive fragment of said OmpC protein.

26. The method of claim 1, wherein the presence or level of said anti-flagellin antibody is determined by assaying the binding between said anti-flagellin antibody and a flagellin protein or an immunoreactive fragment of said flagellin protein.

27. The method of claim 26, wherein said flagellin protein is selected from the group consisting of Cbir-1 flagellin, flagellin X, flagellin A, flagellin B, immunoreactive fragments thereof, and combinations thereof 28. The method of claim 26, wherein said immunoflourescence assay comprises determining the presence or absence of said pANCA in DNAse-treated neutrophils.

29. The method of claim 14, wherein the presence or level of said anti-I2 antibody is determined by assaying the binding between said anti-I2 antibody and an I2 protein or an immunoreactive fragment of said I2 protein.

30. The computer-readable medium of claim 12, wherein said IBD sample is classified as a Crohn's disease (CD) sample or ulcerative colitis (UC) sample.

31. The system of claim 13, wherein said IBD sample is classified as a Crohn's disease (CD) sample or ulcerative colitis (UC) sample.

32. The method of claim 12, wherein said neural network is then applied to said prediction or probability value and the presence or level of said ANCA, ASCA-IgA, ASCA-IgG, anti-OmpC antibody, anti-flagellin antibody, and pANCA to classify said sample as an IBD sample or non-IBD sample.

33. The method of claim 13, wherein said neural network is then applied to said prediction or probability value and the presence or level of said ANCA, ASCA-IgA, ASCA-IgG, anti-OmpC antibody, anti-flagellin antibody, and pANCA to classify said sample as an IBD sample or non-IBD sample.

* * * * *

UNITED STATES PATENT AND TRADEMARK OFFICE
CERTIFICATE OF CORRECTION

| | | |
|---|---|---|
| PATENT NO. | : 7,873,479 B2 | Page 1 of 1 |
| APPLICATION NO. | : 11/565544 | |
| DATED | : January 18, 2011 | |
| INVENTOR(S) | : Augusto Lois and Bruce Neri | |

It is certified that error appears in the above-identified patent and that said Letters Patent is hereby corrected as shown below:

In the Claims:

Column 45, Claim 1, Line 25: please delete

"ANCA, ASCA-IgA, RSCA-IgG, anti-OmpC antibody,"

and replace with

-- ANCA, ASCA-IgA, ASCA-IgG, anti-OmpC antibody, --

Signed and Sealed this
Twenty-fourth Day of May, 2011

David J. Kappos
*Director of the United States Patent and Trademark Office*